US007125998B2

(12) United States Patent
Stossel et al.

(10) Patent No.: US 7,125,998 B2
(45) Date of Patent: *Oct. 24, 2006

(54) RHODIUM AND IRIDIUM COMPLEXES

(75) Inventors: Philipp Stossel, Frankfurt (DE);
Hubert Spreitzer, Viernheim (DE);
Heinrich Becker, Glashütten (DE)

(73) Assignee: Merck Patent GmbH(DE)

( * ) Notice: Subject to any disclaimer, the term of this patent is extended or adjusted under 35 U.S.C. 154(b) by 48 days.

This patent is subject to a terminal disclaimer.

(21) Appl. No.: 10/469,622

(22) PCT Filed: Feb. 21, 2002

(86) PCT No.: PCT/EP02/01841

§ 371 (c)(1),
(2), (4) Date: Mar. 1, 2004

(87) PCT Pub. No.: WO02/068435

PCT Pub. Date: Sep. 6, 2002

(65) Prior Publication Data

US 2004/0138455 A1 Jul. 15, 2004

(30) Foreign Application Priority Data

Feb. 24, 2001 (DE) ............... 101 09 027

(51) Int. Cl.
C07F 15/00 (2006.01)
B32B 15/00 (2006.01)

(52) U.S. Cl. .................. 546/4; 428/689; 428/690; 428/691; 546/2; 546/8; 556/136

(58) Field of Classification Search .............. 546/2, 546/4, 8; 556/136; 428/689, 690, 691
See application file for complete search history.

(56) References Cited

U.S. PATENT DOCUMENTS

| 4,539,507 | A | 9/1985 | Van Slyke et al. | |
|---|---|---|---|---|
| 5,150,006 | A | 9/1992 | Van Slyke et al. | |
| 5,151,629 | A | 9/1992 | VanSlyke | |
| 5,484,922 | A | 1/1996 | Moore et al. | |
| 5,698,858 | A | 12/1997 | Borner | |
| 6,815,091 | B1 * | 11/2004 | Takiguchi et al. | 428/690 |
| 6,821,645 | B1 | 11/2004 | Igarashi et al. | |
| 6,830,828 | B1 | 12/2004 | Thompson et al. | |
| 2002/0121638 | A1 | 9/2002 | Grushin et al. | |

FOREIGN PATENT DOCUMENTS

| EP | 1 175 128 | 1/2002 |
|---|---|---|
| EP | 1 191 613 | 3/2002 |
| JP | 8-319482 | 12/1996 |
| JP | 11-256148 | 9/1999 |
| JP | 11-329739 | 11/1999 |
| WO | WO-02/02714 | 1/2002 |
| WO | WO-02/15645 | 2/2002 |

OTHER PUBLICATIONS

Peter I. Djurovich et al., "Ir(III) Cyclometalated Complexes as Efficient Phosphoresc nt Emitters in Polymer Blend and Organic LEDs," 41(1) Polymer Preprints 770-771, Mar. 2000.
C.H. Chen et al., "Recent Developments in Molecular Organic Electroluminescent Materials," 125 Macromol. Symp. 1-48 (1997), no month.
D.F. O'Brien et al., "Improved Energy Transfer in Electrophosphorescent Devices," 74(3) Appl. Phys. Lett. 442-444, Jan. 1999.
M.A. Baldo et al., "Very High-Efficiency Green Organic Light-Emitting Devices Based on Electrophosphorescence," 75(1) Appl. Phys. Lett. 4-6, Jul. 1999.
Moon-Jay Yang et al., "Organic Light-Emitting Devices Used New Iridium Complexes as Triplet-State Emitter," Preprint for the 61.sup.st Academical Lecture of the Applied Physics Society of Japan, v 3. p. 1117, 6p-ZH-1 (2000), no month.
Sergey Lamansky et al., "Molecularly Doped Polymer Light Emitting Diodes Utilizing Phosphorescent Pt(II) and Ir(III) Dopants," 2 Organic Electronics 53-62 (Mar. 2001).
Vladimir V. Grushin et al., "New, Efficient Electroluminescent Materials Based on Organomettalic Ir Complexes," Chem. Commun. 1494-1495 (Jul. 23, 2001).
Alan Ford et al., "Regioselectivity in Metallation Reactions of 2'-(2-naphthyl)pyridine: 1'-versus 3'-reactivity in Mercuration and Palladation Reactions. Crystal Structure of Chloro(pyridine) [2-(2'-pyridinyl)naphthyl-C.sup.3,N]palladium," 493 J. Organometal. Chem. 215-220 (1995).
Chihaya Adachi et al., "High-Efficiency Organic Electrophosphorescent Devices with Tris(2-phenylpyridine)iridium Doped into Electron-Transporting Materials," 77(6) Appl. Phys. Lett. 904-906 (Aug. 7, 2000).

* cited by examiner

Primary Examiner—Charanjit S. Aulakh
(74) Attorney, Agent, or Firm—Connolly Bove Lodge & Hutz

(57) ABSTRACT

The present invention relates to novel organometallic compounds which are phosphorescence emitters. Compounds of this type can be used as active components (=functional materials) in a series of different types of, application which can be classed within the electronics industry in the broadest sense.

The compounds according to the invention are described by the formulae (I), (Ia), (II), (IIa), (V), (VII), (IX), (XI), (XIII) and (XV).

83 Claims, No Drawings

RHODIUM AND IRIDIUM COMPLEXES

Organometallic compounds, especially compounds of the $d^8$ metals, will find use in the near future as active components (=functional materials) in a series of different types of application which can be classed within the electronics industry in the broadest sense.

The organic electroluminescent devices based on organic components (for a general description of the construction, see U.S. Pat. No. 4,539,507 and U.S. Pat. No. 5,151,629) and their individual components, the organic light-emitting diodes (OLEDs), have already been introduced onto the market, as confirmed by the car radios having organic displays from Pioneer. Further products of this type will shortly be introduced. In spite of this, distinct improvements are still necessary here, in order that these displays provide real competition to the currently market-leading liquid crystal displays (LCDs) or to overtake these.

A development in this direction which has emerged in the last two years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4–6]. For theoretical reasons relating to the spin probability, up to four times the energy efficiency and performance efficiency are possible using organometallic compounds as phosphorescence emitters. Whether this new development will establish itself depends strongly upon whether corresponding device compositions can be found which can also utilize these advantages (triplet emission=phosphorescence compared to single emission=fluorescence) in OLEDs. The essential conditions for practical use are in particular a long operative lifetime, a high stability against thermal stress and a low use and operating voltage, in order to enable mobile applications.

In addition, there has to be efficient chemical access to the corresponding organometallic compounds. In this respect, organorhodium and -iridium compounds are of particular interest. Especially taking into account the cost of rhodium and of iridium, it is of decisive importance in the case of these metals that efficient access is made possible to corresponding derivatives.

5'-Mono-, 5,5"-di- and 5,5",5'"-tri-halogen-functionalized tris-ortho-metalated organorhodium and organoiridium compounds (compounds (I) or (II)), 5',5"-di- and 5',5",5'", 5""-tetra-halogen-functionalized tetrakis-ortho-metalated bridged organorhodium and organoiridium compounds (compound (V) and (VII)) and cationic, neutral or anionic 5'-mono- and 5',5"-di-halogen-functionalized bis-ortho-metalated organorhodium and organoiridium compounds (compound (IX), (XI), (XIII) and (XV)), which form part of the subject-matter of the present invention, will be central key building blocks for obtaining highly efficient triplet emitters, since the halogen function can be converted to a multitude of functions with the aid of common methods described in the literature. This enables not only the covalent incorporation of these active, light-emitting centers into a multitude of polymers, but also the tailoring of the optoelectronic properties of these building blocks. For instance, starting from the structures mentioned, typical C—C bond-forming reactions (e.g. Stille or Suzuki coupling), or else C-heteroatom bond-forming reactions (e.g. for C—N: Hartwig-Buchwald coupling, similarly also for C—O and C—P) are possible, in order thus to further functionalize the halogen-functionalized compounds, or use them as (co) monomers in the preparation of corresponding polymers.

5'-Mono-, 5,5"-di- and 5,5",5'"-tri-halogen-functionalized tris-ortho-metalated organorhodium and organoiridium compounds (compounds (I) or (II)), 5',5"-di- and 5',5",5'", 5""-tetra-halogen-functionalized tetrakis-ortho-metalated bridged organorhodium and organoiridium compounds (compound (V) and (VII)) and cationic, neutral or anionic 5'-mono- and 5',5"-di-halogen-functionalized bis-ortho-metalated organorhodium and organoiridium compounds (compound (IX), (XI), (XIII) and (XV)) have hitherto not been described in the literature, even though their efficient preparation and availability as pure materials is of great significance for various electrooptical applications.

The nearest prior art may be regarded as being the monobromination and monoiodination of a cationic ruthenium(II) complex which, in addition to the orthometalated 2-phenylpyridine ligands, also bears 2,2'-bipyridine ligands [C. Coudret, S. Fraysse, J.-P-Launay, Chem. Commun., 1998, 663–664]. The brominating agent used is N-bromosuccinimide, and the iodinating agent a mixture of iodobenzene diacetate and elemental iodine in a molar ratio of one to one. The isolated yield after chromatographic purification in the case of bromination is quoted as 95%, and in the case of iodination as 50%.

An analogous reaction may be regarded as being the bromination described by Clark et al. of orthometalated 2-phenylquinoline and 2,3-diphenylquinoxaline ligands of ruthenium(II) carbonyl chloro and osmium(II) carbonyl chloro complexes with pyridinium perbromide. After chromatographic purification, yields of from 27% to 92% were obtained [A. M. Clark, C. E. F. Rickard, W. R. Roper, L. J. Wright J. Organomet. Chem., 2000, 598, 262–275].

These two references have the following disadvantages:
(1) Only the derivatization of Ru or Os complexes, but not that of Rh or Ir compounds are described.
(2) No viable teaching is provided as to how, in the presence of a plurality of substituted positions, it is possible to selectively obtain the desired mono-, or di-, or tri- or tetra-functionalized compounds, since in both cases only one halogenation per complex molecule is possible.

In contrast, the selective 5'-mono-, 5',5"-di-, 5',5",5'"-tri- and 5',5",5'",5""-tetrahalogenation of bis-, tris- or tetrakis-orthometalated organorhodium or organoiridium compounds has hitherto not been described in the literature.

It has now been found that, surprisingly, the novel compounds (I) or (II), according to scheme 1, are obtained starting from tris-ortho-metalated organorhodium or organoiridium compounds, and that the novel compounds (V) or (VII), according to scheme 2, are obtained starting from tetrakis-ortho-metalated bridged organorhodium and organoiridium compounds, and that the novel compounds (IX), (XI), (XIII) or (XV), according to scheme 3, are obtained starting from cationic, neutral or anionic functionalized bis-ortho-metalated organorhodium and organoiridium compounds, with a halogen or interhalogen, in the presence of a base and optionally of a Lewis acid, or of an organic N-halogen compound or of a halogenating agent consisting of an organic O-halogen compound and a halogen $X_2$, with suitable choice of the stoichiometric ratio of the corresponding halogenating agent, to give the compounds (III), (IV), (VI), (VIII), (X), (XII), (XIV) or (XVI) and also with suitable choice of the reaction parameters such as reaction temperature, reaction medium, concentration and reaction times, reproducibly in about 90–98% yield, without using chromatographic purification methods, in purities of >99% by NMR or HPLC (see examples 1 to 10).

The above-described process is notable for three features which have hitherto not been described in this form in the literature:

First, the selective 5'-mono-, 5',5'''-di-, 5',5'',5'''-tri and 5',5'',5''',5''''-tetra-halogenation is unexpected and unknown in this form. It is presumed to result from the activity that the para-position to the rhodium or iridium atom experiences as a consequence of the metal. The unexpectedly high activity of this position toward an electrophilic substitution, in this case halogenation, is deliberately exploited by the use of mild halogenating agents.

A decisive factor for the achievement of high selectivities and high reaction rates is to work in the presence of an acid-binding agent which binds the hydrohalic acid formed in the course of substitution. This is a surprising finding which apparently effectively suppresses the side reactions. The halogenating agents according to the invention therefore comprise an acid-binding agent, such as a base, which is either an intrinsic constituent of the halogenating agent or is added additionally to the halogenating agent.

Secondly, the high conversion achieved, which is reflected in the reproducibly very good yields of isolated product, is unexpected and unique for the halogenation of ortho-metalated ligands bonded to metals of the iron triad.

Thirdly, the compounds obtained occur, without complicated chromatographic purification, in very good purities of >99% by NMR or HPLC. This is essential for use in optoelectronic components, or the utilization as intermediates for the preparation of corresponding compounds.

As outlined above, the compounds according to the invention have not been described to date and are therefore novel.

The present invention therefore provides the compounds (I) and (II) according to scheme 1 where the symbols and indices are defined as follows:

M is Rh, Ir

X is F, Cl, Br, I

Y is O, S, Se

R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups may be replaced by —O—, —S—, —$NR^1$— or —$CONR^2$— and in which one or more hydrogen atoms may be replaced by F, or an aryl or heteroaryl group having from 4 to 14 carbon atoms which may be substituted by one or more nonaromatic R radicals; and a plurality of R substituents, either on the same ring or on the two different rings together may in turn encompass a further mono- or polycyclic ring system;

$R^1$ and $R^2$ are the same or different and are each H or an aliphatic or aromatic hydrocarbon radical having 1 to 20 carbon atoms, a is 0, 1, 2, 3 or 4, preferably 0, 1 or 2, b is 0, 1, 2 or 3, preferably 0 or 1, n is 1, 2 or 3.

A further embodiment of the invention relates to those Rh and Ir complexes which at the same time have ligands of the type such as in the case of compounds (I) and those of compounds (II), i.e. mixed ligand systems. These are described by the formulae (Ia) and (IIIa):

Scheme 1:

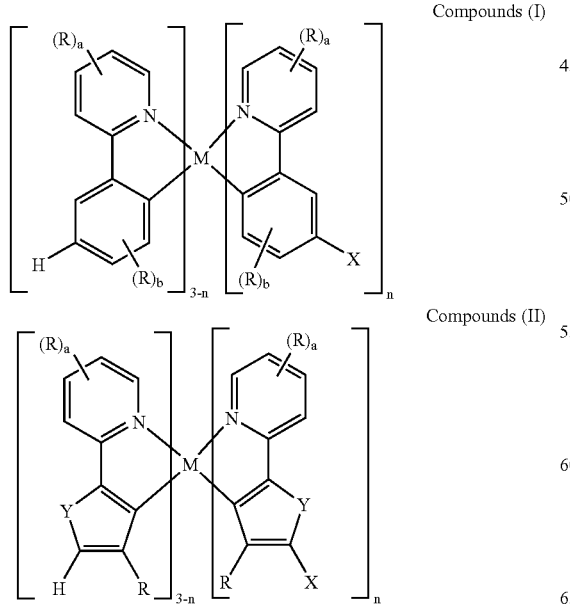

Compounds (I)

Compounds (II)

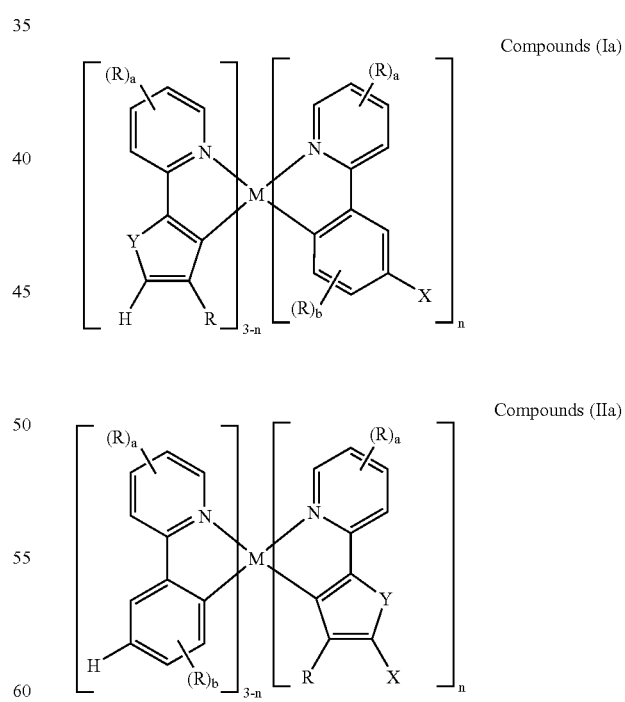

Compounds (Ia)

Compounds (IIa)

where the symbols and indices are as defined under the formulae (I) and (II).

The present invention therefore likewise provides the compounds (V) and (VII) according to scheme 2

Scheme 2:

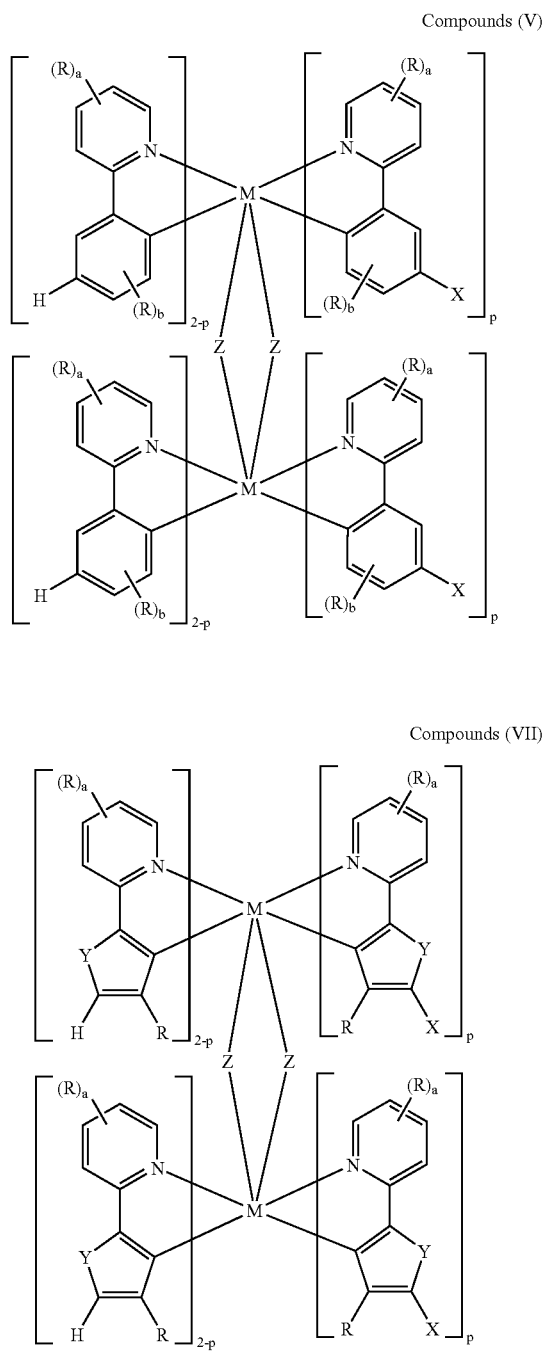

Compounds (V)

Compounds (VII)

where the symbols and indices are defined as follows:
M is Rh, Ir
X is F, Cl, Br, I
Y is O, S, Se
Z is F, Cl, Br, I, O—$R^1$, S—$R^1$, N($R^1$)$_2$
R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups may be replaced by —O—, —S—, —$NR^1$— or —$CONR^2$— and in which one or more hydrogen atoms may be replaced by F, or an aryl or heteroaryl group having from 4 to 14 carbon atoms which may be substituted by one or more nonaromatic R radicals; and a plurality of R substituents, either on the same ring or on the two different rings together in turn may encompass a further mono- or polycyclic ring system;

$R^1$ and $R^2$ are the same or different and are each H or an aliphatic or aromatic hydrocarbon radical having 1 to 20 carbon atoms, a is 0, 1, 2, 3 or 4, preferably 0, 1 or 2, b is 0, 1, 2 or 3, preferably 0 or 1, p is 1 or 2.

The present invention therefore likewise provides the compounds (IX), (XI), (XIII) and (XV) according to scheme 3

Scheme 3:

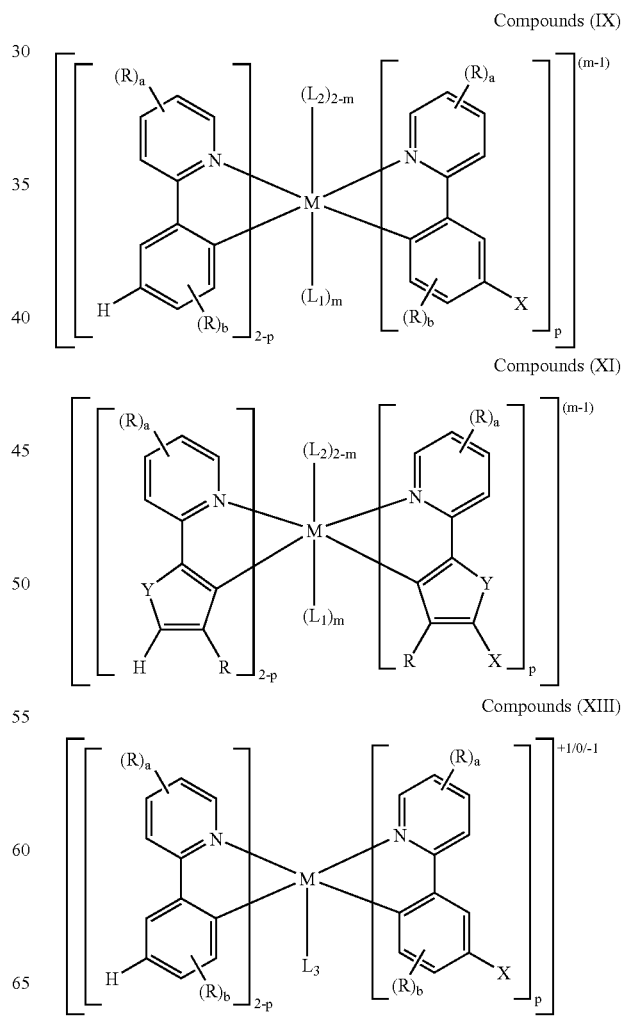

Compounds (IX)

Compounds (XI)

Compounds (XIII)

Compounds (XV)

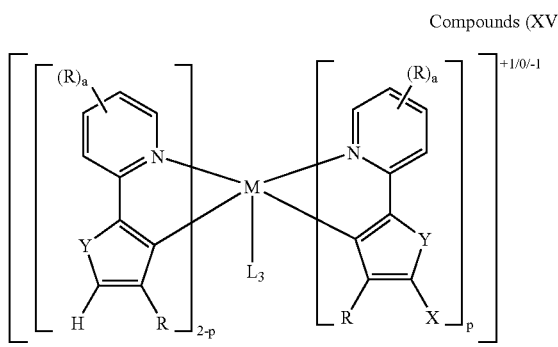

where the symbols and indices are defined as follows:

M is Rh, Ir
X is F, Cl, Br, I
Y is O, S, Se
R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups may be replaced by —O—, —S—, —$NR^1$— or —$CONR^2$— and in which one or more hydrogen atoms may be replaced by F, or an aryl or heteroaryl group having from 4 to 14 carbon atoms which may be substituted by one or more nonaromatic R radicals; and a plurality of R substituents, either on the same ring or on the two different rings together in turn may encompass a further mono- or polycyclic ring system;
$R^1$ and $R^2$ are the same or different and are H or an aliphatic or aromatic hydrocarbon radical having 1 to 20 carbon atoms,
$L_1$ is a neutral, monodentate ligand
$L_2$ is a monoanionic, monodentate ligand
$L_3$ is a neutral or mono- or dianionic bidentate ligand,
a is 0, 1, 2, 3 or 4, preferably 0, 1 or 2,
b is 0, 1, 2 or 3, preferably 0 or 1,
m is 0, 1 or 2,
p is 1 or 2.

The neutral, monodentate ligands $L_1$ according to the invention are carbon monoxide, isonitriles, e.g. tert-butylisonitrile, cyclohexylisonitrile, adamantylisonitrile, amines, e.g. trimethylamine, triethylamine, morpholine, phosphines, e.g. trifluorophosphine, trimethylphosphine, tricyclohexylphosphine, tri-tert-butylphosphine, triphenylphosphine, tris(pentafluorophenyl)phosphine, phosphites, e.g. trimethyl phosphite, triethyl phosphite, arsines, e.g. trifluoroarsine, trimethylarsine, tricyclohexylarsine, tri-tert-butylarsine, triphenylarsinine, tris(pentafluorophenyl)arsine, stibines, e.g. trifluorostibine, trimethylstibine, tricyclohexylstibine, tri-tert-butylstibine, triphenylstibine, tris(pentafluorophenyl)stibine and nitrogen heterocycles such as pyridine, pyridazine, pyrazine, triazine.

Monoanionic, monodentate ligands $L_2$ according to the invention are halides, cyanide, cyanate, isocyanate, thiocyanate, isothiocyanate, alkoxides, e.g. methoxide, ethoxide, propoxide, isopropoxide, tert-butoxide, phenoxide, thioalkoxides, e.g. methanethiolate, ethanethiolate, propanethiolate, iso-propanethiolate, tert-thiobutoxide, thiophenoxide, amides e.g. dimethylamide, diethylamide, diisopropylamide, pyrrolide, morpholide, carboxylates e.g. acetate, trifluoroacetate, propionate, benzoate or anionic nitrogen heterocycles such as pyrrolide, imidazolide, pyrazolide.

Neutral or mono- or dianionic, bidentate ligands $L_3$ according to the invention are diamines, e.g. ethylenediamine, N,N,N',N'-tetramethylethylenediamine, propylenediamine, N,N,N', N'-tetramethylpropylenediamine, cis-, trans-diaminocyclohexane, cis-, trans-N,N,N',N'-tetramethyldiaminocyclohexane, imines, e.g. 2[(1-(phenylimino)ethyl]pyridine, 2[(1-(2-methylphenylimino)ethyl]pyridine, 2[(1-(2,6-di-iso-propylphenylimino)ethyl]pyridine, 2[(1-(methylimino)ethyl]-pyridine, 2[(1-(ethylimino)ethyl]pyridine, 2[(1-(iso-propylimino)ethyl]pyridine, 2[(1-(tert-butylimino)ethyl]pyridine, diimines, e.g. 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-diisopropylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, e.g. 2,2'-bipyridine, o-phenanthroline, diphosphines, e.g. bis(diphenylphosphino)methane, bis(diphenylphosphino)ethane, bis(diphenylphosphino)propane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, e.g. acetylacetone, benzoylacetone, 1,5-diphenylacetylacetone, dibenzoylmethane, bis(1,1,1-trifluoroacetyl)methane, 3-ketonates derived from 3-keto esters, e.g. ethyl acetoacetate, carboxylates derived from amino carboxylic acids, e.g. pyridine-2-carboxylic acid, quinoline-2-carboxylic acid, glycine, dimethylglycine, alanine, dimethylaminoalanine, salicyliminates derived from salicylimines, e.g. methylsalicylimine, ethylsalicylimine, phenylsalicylimine, dialkoxides derived from dialcohols, e.g. ethylene glycol, 1,3-propylene glycol, ditholates derived from dithiols, e.g. 1,2-ethylenedithiol, 1,3-propylenedithiol.

The present invention further provides processes for preparing the compounds (I) and (II), by reacting the compounds (III) or (IV)

Compounds (III)

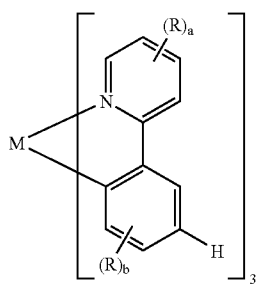

Compounds (IV)

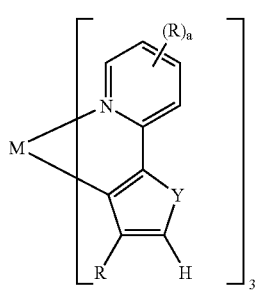

where M and the radicals and indices Y, R, a and b are as defined above with halogenating agents.

The present invention further provides processes for preparing the compounds (V) and (VII), by reacting the compounds (VI) or (VIII)

Compounds (VI)

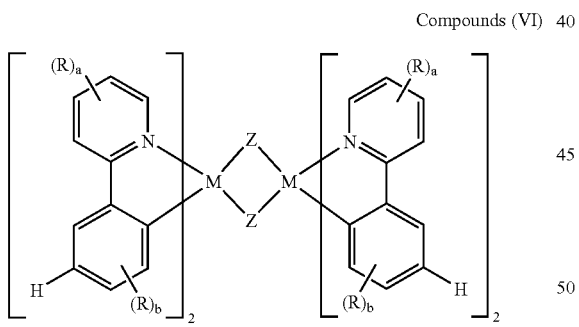

Compounds (VIII)

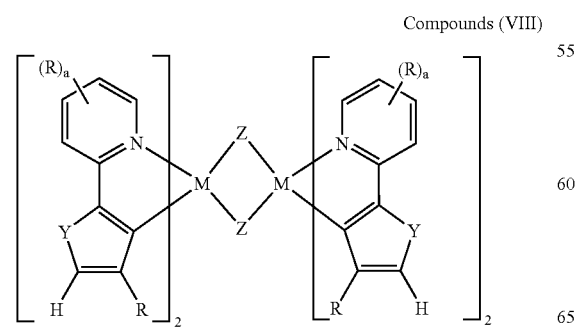

where M and the radicals and indices Z, Y, R, a and b are as defined above with halogenating agents.

The present invention further provides processes for preparing the compounds (IX), (XI), (XIII) and (XV), by reacting the compounds (X), (XII), (XIV) or (XVI)

Compounds (X)

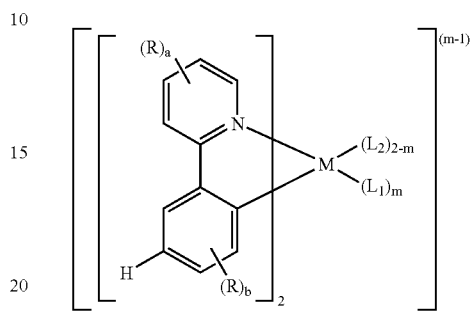

Compounds (XII)

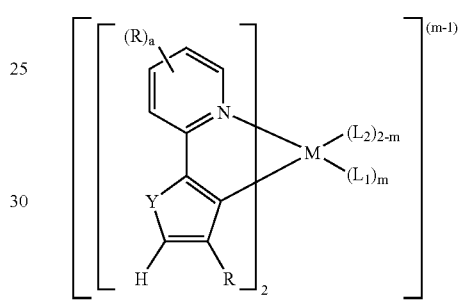

Compounds (XIV)

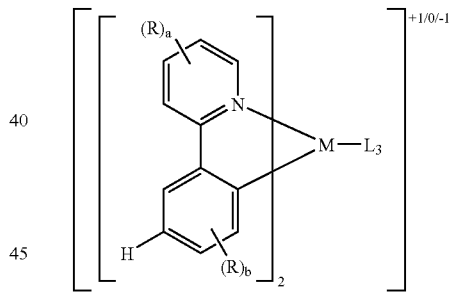

Compounds (XVI)

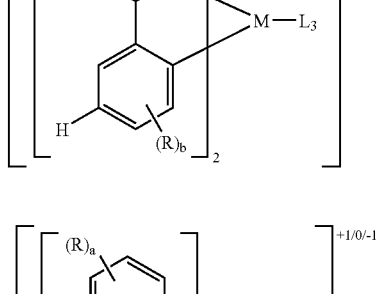

where M and the radicals and indices $L_1$, $L_2$, $L_3$, Y, R, a, b and m are as defined above with halogenating agents.

The process according to the invention is illustrated by scheme 4:

Scheme 4:
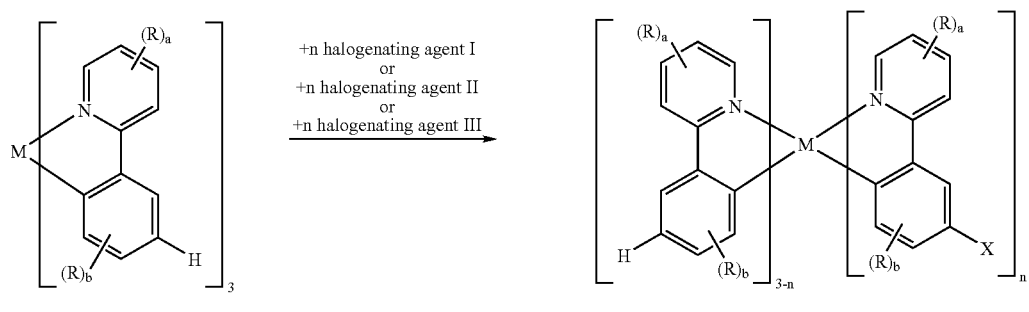
Compounds (III) → Compounds (I)
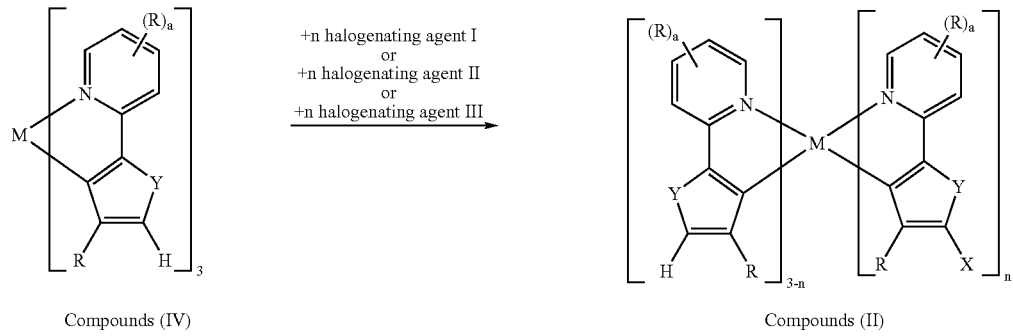
Compounds (IV) → Compounds (II)
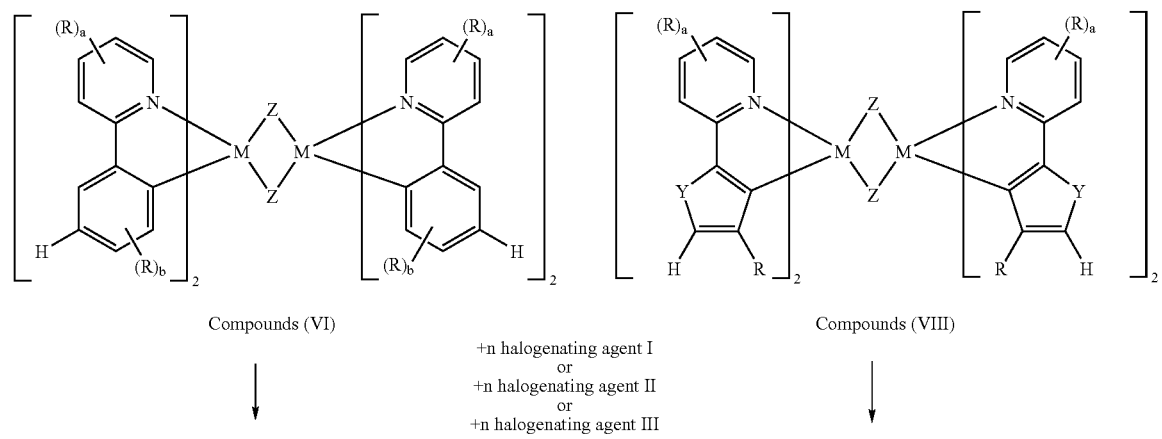
Compounds (VI)　　　　　　　Compounds (VIII)

-continued
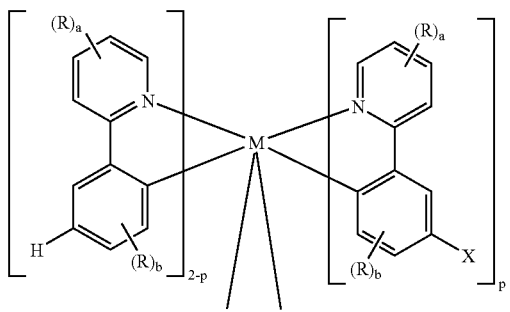
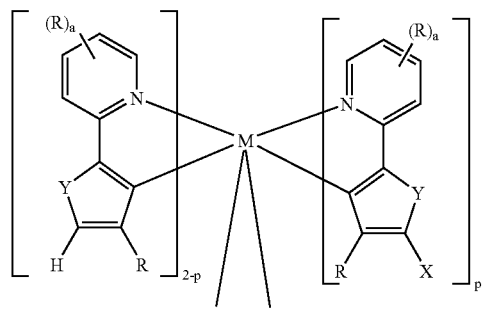
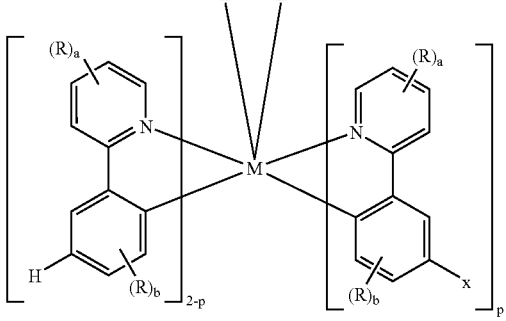
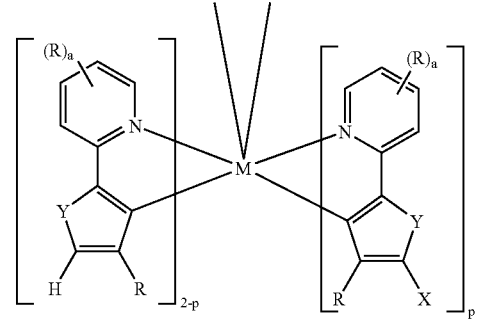
Compounds (V)                    Compounds (VII)
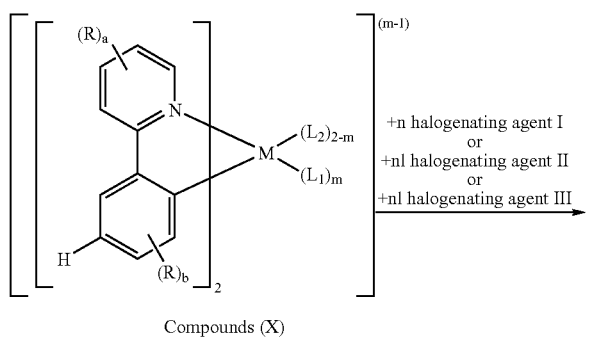
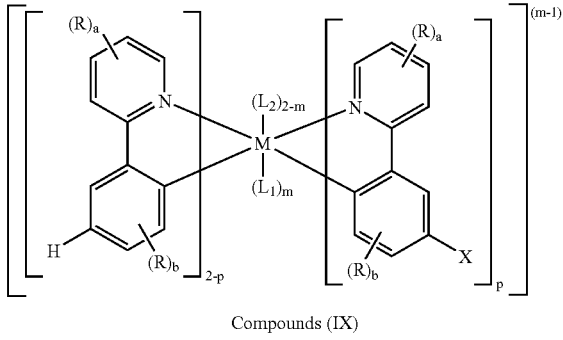
Compounds (X)                    Compounds (IX)
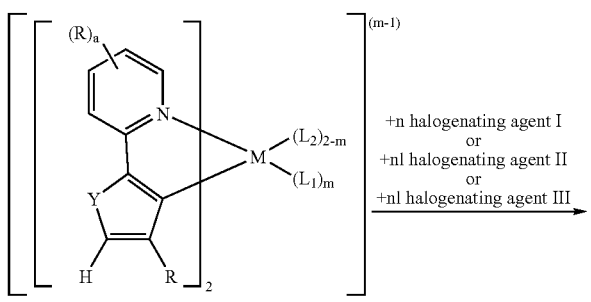
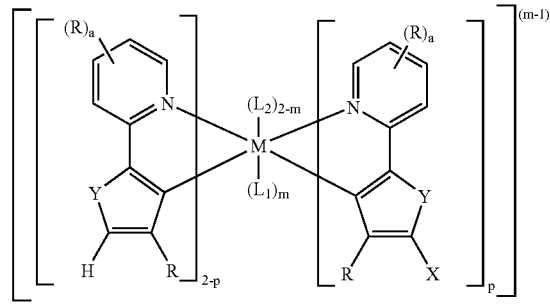
Compounds (XII)                  Compounds (XI)
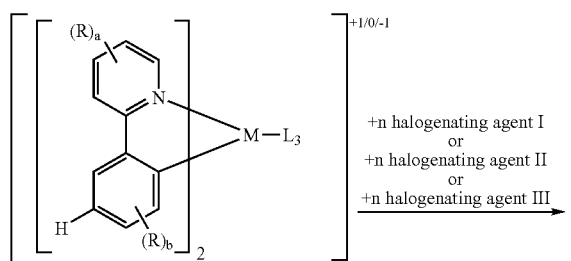
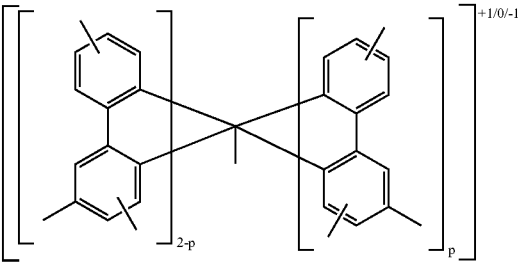
Compounds (XIV)                  Compounds (XIII)

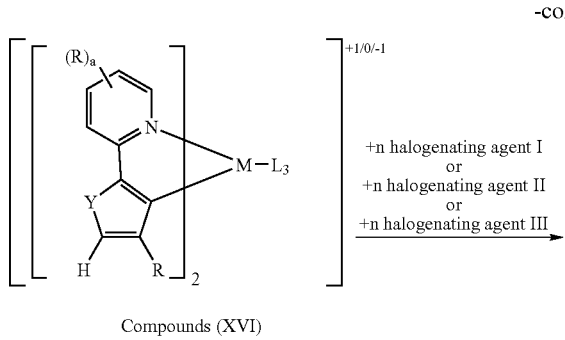

Compounds (XVI)

+n halogenating agent I
or
+n halogenating agent II
or
+n halogenating agent III
→

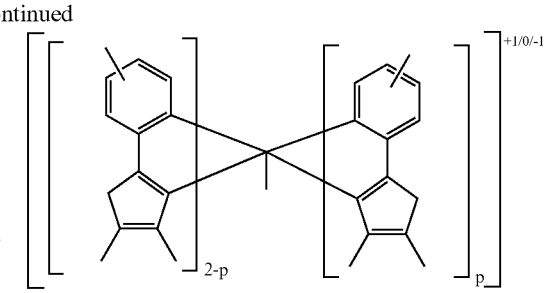

Compounds (XV)

Halogenating agents according to the invention are the halogens $X_2$ or the interhalogens X—X and a base in a ratio of from 1:1 to 1:100 and optionally a Lewis acid in a ratio (halogen to Lewis acid) of from 1:0.1 to 1:0.0001, for example chlorine, bromine or iodine, or chlorine fluoride, bromine fluoride, iodine fluoride, bromine chloride, iodine chloride or iodine bromide, in combination with organic bases such as amines, for example triethylamine, tri-n-butylamine, diisopropylethylamine, morpholine, N-methylmorpholine and pyridine, or salts of carboxylic acids such as sodium acetate, sodium propionate, sodium benzoate, or inorganic bases such as sodium or potassium phosphate or hydrogenphosphate, potassium or sodium hydrogencarbonate, potassium or sodium carbonate, or else organic bromine complexes such as pyridinium perbromide, optionally each in combination with a Lewis acid, e.g. boron trifluoride, boron trifluoride etherate, boron trichloride, boron tribromide, boron triiodide, aluminum trichloride, aluminum tribromide, aluminum triiodide, iron(III) chloride, iron(III) bromide, zinc(II) chloride, zinc(II) bromide, tin(IV) chloride, tin(IV) bromide, phosphorus pentachloride, arsenic pentachloride and antimony pentachloride are used.

These halogenating agents are referred to hereinbelow as halogenating agents (I).

Further halogenating agents according to the invention are organic N—X compounds, such as 1-(chloromethyl)-4-fluoro-1,4-diazoniabicyclo[2.2.2]octane bis(tetrafluoroborate), N-halocarboxamides such as N-chloro-, N-bromo- and N-iodoacetamide, N-chloro-, N-bromo- and N-iodopropionamide, N-chloro-, N-bromo- and N-iodobenzamide, or N-halocarboximides such as N-chloro-, N-bromo- and N-iodosuccinimide, N-chloro-, N-bromo- and N-iodophthalimide, or N-dihalosulfonamides such as benzenesulfo-N-dibromamide, or N-halosulfonamide salts such as chloramine B or T.

These halogenating agents are referred to hereinbelow as halogenating agents (II).

In the case of the halogenating agents (II), the additive use of Lewis acids, as listed above, for example, may likewise be advantageous.

Still further halogenating agents according to the invention are organic O—X compounds and halogens $X_2$ in a molar ratio of from 0.5:1 to 1:1, such as iodoaryl dicarboxylates in a molar ratio of from 0.5:1 to 1:1 with a halogen $X_2$, for example iodobenzene diacetate or bistrifluoroacetoxyiodobenzene and elemental bromine in a molar ratio of from 0.5:1 to 1:1, or iodobenzene diacetate or bistrifluoroacetoxyiodobenzene and elemental iodine in a molar ratio of from 0.5:1 to 1:1.

These halogenating agents are referred to hereinbelow as halogenating agents (III).

In the process according to the invention, a stoichiometric ratio of the halogenating agents (I), (II) or (III), based on the content of active halogen, to the compounds (III), (IV), (X), (XII), (XIV) or (XVI) of 1:1 leads selectively to the compounds (I), (II) where n=1 and (IX), (XI), (XIII) or (XV) where p=1. This is a surprising and unforeseeable result.

In the process according to the invention, a stoichiometric ratio of the halogenating agents (I), (II) or (III), based on the content of active halogen, to the compounds (III), (IV), (VI), (VIII), (X), (XII), (XIV) or (XVI) of 2:1 leads selectively to the compounds (V) or (VII) where p=1 and (I) or (II) where n=2 and (IX), (XI), (XIII) or (XV) where p=2. This is a surprising and unforeseeable result.

In the process according to the invention, a stoichiometric ratio of the halogenating agents (I), (II) or (III), based on the content of active halogen, to the compounds (III) or (IV) of 3:1 leads selectively to the compounds (I) or (II) where n=3. This is a surprising and unforeseeable result.

In the process according to the invention, a stoichiometric ratio of the halogenating agents (I), (II) or (III), based on the content of active halogen, to the compounds (VI) or (VIII) of from 4:1 to 1000:1 leads selectively to the compounds (V) or (VII) where p=2. This is a surprising and unforeseeable result.

The stoichiometric ratios described here are preferred embodiments of the present invention, since they lead to uniformly substituted products. It will be appreciated that slight deviations from the abovementioned ratios still lead to good to acceptable results.

According to the invention, a reducing agent may optionally be added to the reaction mixture in a molar ratio of from 0.1:1 to 10:1, based on the compounds (III), (IV), (VI), (VIII), (X), (XII), (XIV) or (XVI). Reducing agents according to the invention are hydrazine and hydroquinones, for example hydroquinone or tetrachlorohydroquinone, 2,3-dichloro-5,6-dicyanohydroquinone.

Reaction media according to the invention are protic or aprotic, halogen-free or halogenated solvents, for example alcohols such as methanol, ethanol, propanol, butanol, polyhydric alcohols such as ethylene glycol, propylene glycol, nitriles such as acetonitrile, propionitrile or benzonitrile, ethers such as diethyl ether, THF or dioxane, aromatic hydrocarbons such as benzonitrile, nitrobenzene or chlorobenzene, N,N-dialkylamides such as dimethylformamide, methylacetamide or N-methylpyrroldinone, sulfoxides such as dimethyl sulfoxide, sulfones such as dimethylsulfone or sulfolane, halogenated hydrocarbons such as dichloromethane, trichloromethane, 1,1-dichloroethane, 1,2- dichloroethane, 1,1,2,2-tetrachloroethane, although preference is given to aromatic or chlorinated solvents.

According to the invention, the reaction is carried out in the temperature range from −78° C. to 150° C., preferably at from 0° C. to 100° C., very preferably at from 10° C. to 60° C.

According to the invention, the concentration of the rhodium or iridium reactant to compounds (III), (IV), (VI), (VIII), (X), (XII), (XIV) or (XVI) is in the range from 0.0005 mol/l to 2 mol/l, more preferably in the range from 0.002 mol/l to 0.1 mol/l.

According to the invention, the rhodium or iridium reactants may be dissolved or suspended in the reaction medium.

According to the invention, the reaction is carried out within from 10 minutes up to 100 hours, preferably within from 1 h to 40 h.

The synthesis methods illustrated here can be used for compounds (I), (II), (Ia), (IIa), (V), (VII), (IX), (XI), (XIII) or (XV), inter alia, in the examples adduced hereinbelow.

Example 1

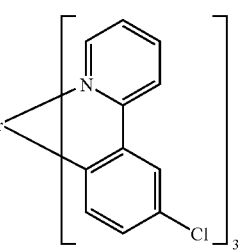

Example 2

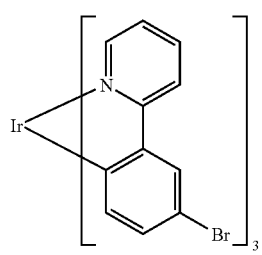

Example 3

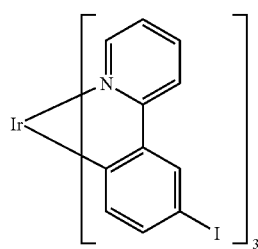

Example 4

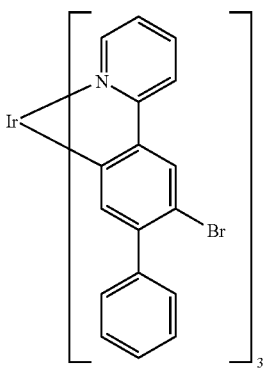

Example 5

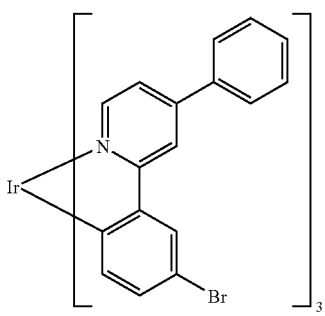

Example 6

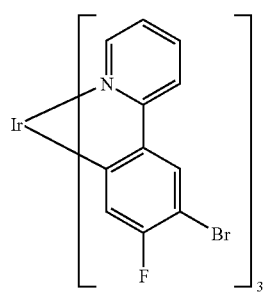

Example 7

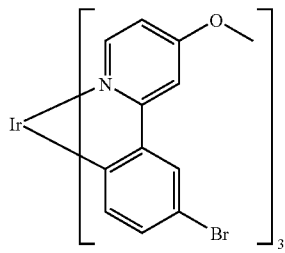

Example 8

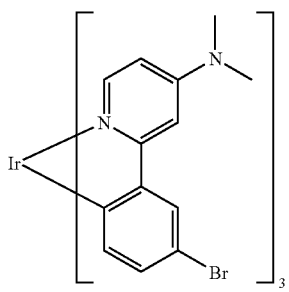

Example 9

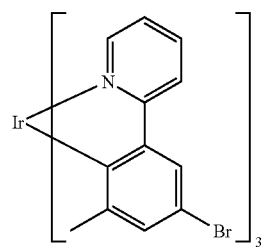

-continued
Example 10
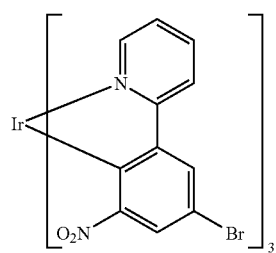
Example 11
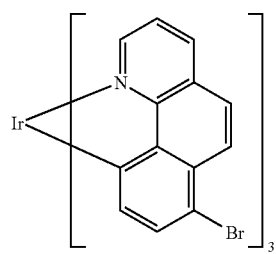
Example 12
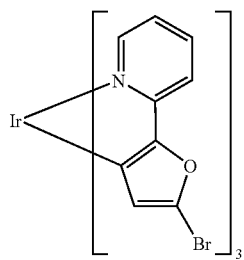
Example 13
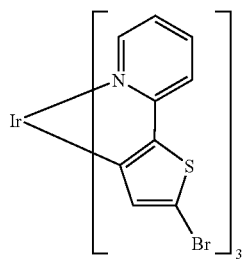
Example 14
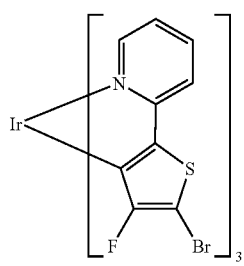
Example 15
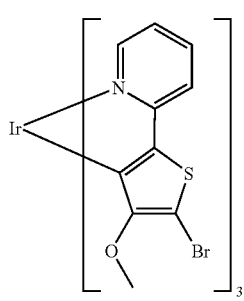
-continued
Example 16
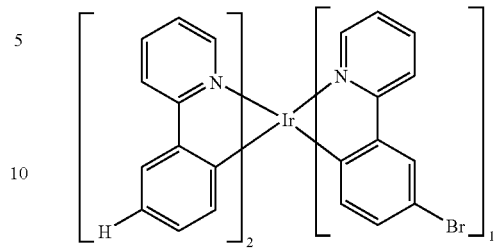
Example 17
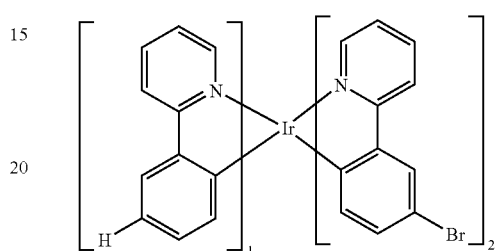
Example 18
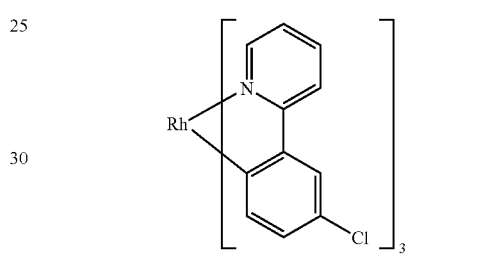
Example 19
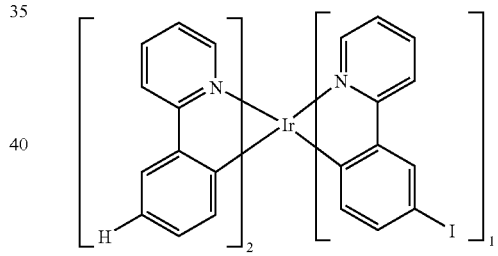
Example 20
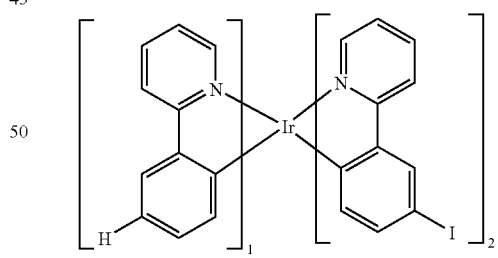
Example 21
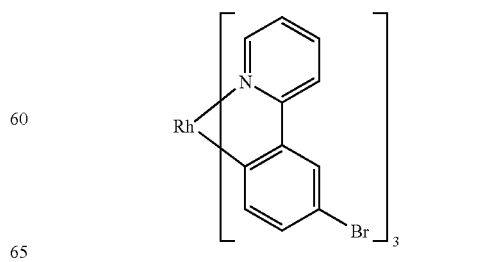

Example 22
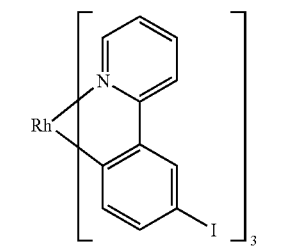
Example 23
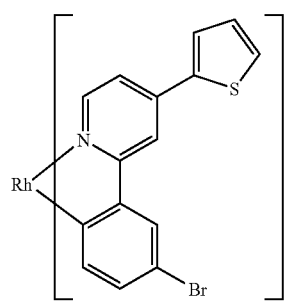
Example 24
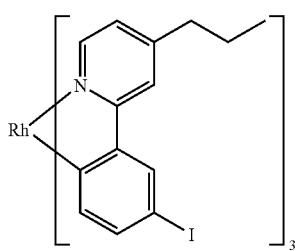
Example 25
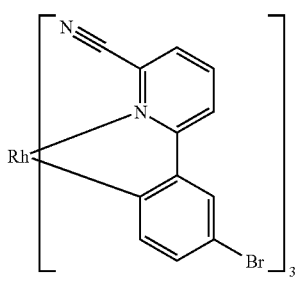
Example 26
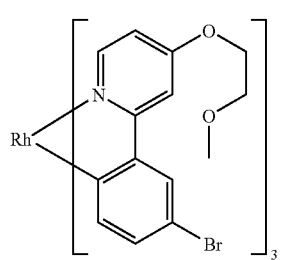
Example 26
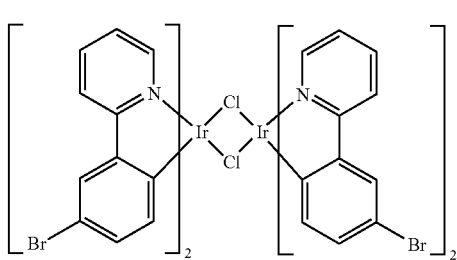
Example 27
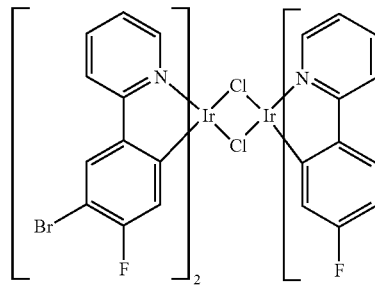
Example 28
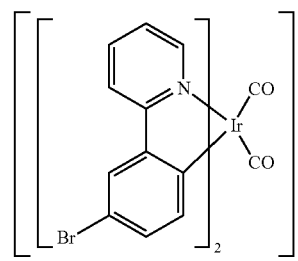
Example 29
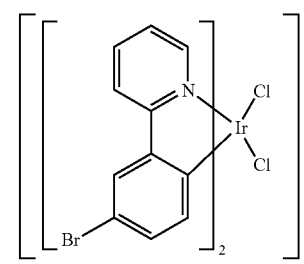
Example 30
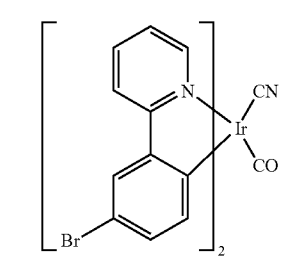
Example 31
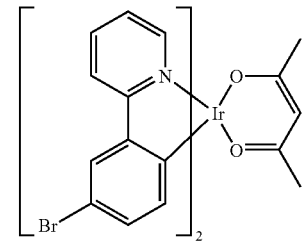
Example 32
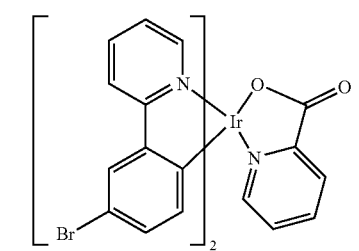

-continued

Example 33

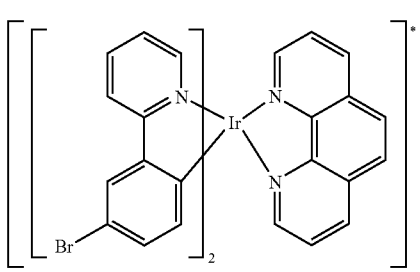

The compounds according to the invention obtained in this way can then find use, for example, as comonomers for obtaining corresponding conjugated or else semiconjugated polymers. For instance, they may be incorporated by polymerization, inter alia, into soluble polyfluorenes (for example according to EP-A-842208 or WO 00/22026), poly-spiro-bifluorenes (for example according to EP-A-707020), poly-para-phenylenes (for example according to WO 92/18552), polycarbazoles or else polythiophenes (for example according to EP-A-1028136).

The polyfluorenes disclosed in EP-A-842208 and WO 00/22026 form part of this description.

Poly-spiro-bifluorenes dislcosed in EP-A-707020 form part of this description.

The poly-para-phenylenes disclosed in WO 92/18552 form part of this description.

The polythiophenes disclosed in EP-A-1028136 form part of this description.

The compounds according to the invention may of course also be further functionalized by, for example, the above-mentioned reaction types, and thus be converted to extended low molecular weights Rh or Ir complexes. Examples are the functionalization with arylboronic acids according to SUZUKI or with amines according to HARTWIG-BUCHWALD.

The present invention is illustrated by the examples which follow, without any intention to restrict it to them. Those skilled in the art can prepare further complexes according to the invention from the explanations without any inventive activity or employ the process according to the invention.

1. Synthesis of Symmetrically and Asymmetrically Functionalized tris-ortho-metalated organorhodium or organoiridium Compounds:

The syntheses which follow were, unless stated otherwise, carried out under air using commercial solvent. The reactants were obtained from ALDRICH [bromine, iodine, N-chlorosuccinimide, N-bromosuccinimide, N-ethyldiisopropylamine, iron(III) chloride, iodobenzene diacetate, hydroquinone]. Before using the N-haloimides and iodobenzene diacetate, the content of active halogen was determined iodometrically [in a similar manner to: K. W. Rosenmund, W. Kuhnhenn, Ber. 1923, 56, 1262]. fac-Tris[2-(2-pyridinyl-κN)phenyl-κC]iridium(III), fac-tris[2-(2-pyridinyl-κN)4-fluorophenyl-κC]iridium(III) and)fac-tris[2-(2-pyridinyl-κN)-4-methoxyphenyl-κC]iridium(III) were prepared as described in the unpublished application DE 10104426.7. Tetrakis[(2-pyridinyl-κN)phenyl-κC][di-μ-chloro]diiridium (III) was prepared by literature methods (S. Sprouse, K. A. King, P. J. Spellane, R. J. Watts J. Am. Chem. Soc. 1984, 106, 6647).

The assignment of the $^1$H NMR signals was supported partly by H—H COSY spectra, and those of the $^{13}$C{$^1$H} NMR signals each via DEPT-135 spectra.

Numbering scheme for the assignment of the $^1$H NMR signals [according to C. Coudret, S. Fraysse, J.-P-Launay, Chem. Commun., 1998, 663–664]:

Scheme 3:

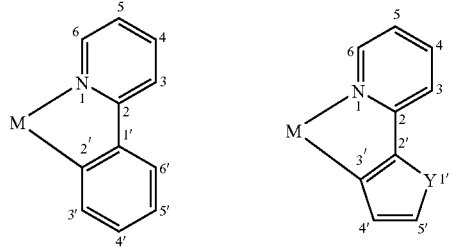

EXAMPLE 1 fac-Tris[2-(2-pyridinyl-κN)(5-chlorophenyl)-κC] iridium(III)

4.407 g (33.0 mmol) of N-chlorosuccinimide were added with the exclusion of light to an efficently stirred solution of 6.548 g (10.0 mmol) of fac-tris[2-(2-pyridinyl-κN)phenyl-κC]iridium(III) in 1500 ml dichloromethane. The reaction mixture was stirred at room temperature for a further 20 h. After concentrating under reduced pressure to a volume of 50 ml, the solution was admixed with 500 ml of ethanol. Subsequently, the microcrystalline precipitate was filtered off (P4), washed three times with 50 ml of ethanol and then dried under reduced pressure (60° C., $10^{-4}$ mbar). The yield, at a purity of >99.7% by $^1$H NMR, was 7.210–7.356 g, corresponding to 95.1–97.0%.

$^1$H NMR (DMSO-d6): [ppm]=8.32 (br. dd, 1 H, $^3$J$_{HH}$=8.4 Hz, $^4$J$_{HH}$=1.3 Hz, H6), 7.91 (d, 1 H, $^4$J$_{HH}$=2.0 Hz, H6'), 7.87 (ddd, 1 H, $^3$J$_{HH}$=8.4 Hz, $^3$J$_{HH}$=8.4 Hz, $^4$J$_{HH}$=1.6 Hz, H5), 7.42 (dd, 1 H, $^3$J$_{HH}$=5.4 Hz, $^4$J$_{HH}$=1.6 Hz, H3), 7.26 (ddd, 1 H, $^3$J$_{HH}$=8.4 Hz, $^3$J$_{HH}$=5.4 Hz, $^4$J$_{HH}$=1.3 Hz, H4), 6.87 (dd, 1 H, $^3$J$_{HH}$=8.0 Hz, $^4$J$_{HH}$=2.0 Hz, H4'), 6.63 (d, 1 H, $^3$J$_{HH}$=8.0 Hz, H3').

EXAMPLE 2 fac-Bis[2-(2-pyridinyl-κN)phenyl-κC]-[2-(2-pyridinyl-κN)(5-bromophenyl)-κC]iridium(III)

With the exclusion of light, a solution of 1.816 g (10.2 mmol) of N-bromosuccinimide (content of active bromine: 98%) in 100 ml dichloromethane was added dropwise over 1 h to an efficiently stirred solution of 6.548 g (10.0 mmol) of fac-tris[2-(2-pyridinyl-κN)phenyl-κC]iridium(III) in 1500 ml of dichloromethane. The solution was stirred at room temperature for a further 15 h. After concentrating under reduced pressure to a volume of 100 ml, the solution was admixed with 500 ml of ethanol. Subsequently, the microcrystalline precipitate was filtered off (P4), washed three times with 50 ml of ethanol and then dried under reduced pressure (60° C., $10^{-4}$ mbar). The yield, at a purity of >99.7% by $^1$H NMR, was 7.138–7.197 g, corresponding to 97.2–98.1%.

$^1$H NMR (DMSO-d6): [ppm]=8.25–8.22 (m, 1 H), 8.16–8.12 (m, 2 H), 7.95–7.93 (m, 1 H), 7.86–7.74 (m, 5 H), 7.52–7.45 (m, 3 H), 7.21–7.17 (m, 1 H), 7.16–7.11 (m, 2 H), 6.89–6.78 (m, 3 H), 6.75–6.53 (m, 5 H).

EXAMPLE 3 fac-[2-(2-pyridinyl-κN)phenyl-κC]-bis[2-(2-pyridinyl-κN)(5-bromophenyl)-κC]iridium(III)

With the exclusion of light, a solution of 3.632 g (20.4 mmol) of N-bromosuccinimide (content of active bromine: 98%) in 100 ml dichloromethane was added dropwise over 1 h to an efficiently stirred solution of 6.548 g (10.0 mmol) of fac-tris[2-(2-pyridinyl-κN)phenyl-κC]iridium(III). The solution was stirred at room temperature for a further 15 h. After concentrating under reduced pressure to a volume of 100 ml, the solution was admixed with 500 ml of ethanol. Subsequently the microcrystalline precipitate was filtered off (P4), washed three times with 50 ml of ethanol and then dried under reduced pressure (60° C., $10^{-4}$ mbar). The yield, at a purity of >99.7% by $^1$H NMR, was 7.858–7.907 g, corresponding to 96.7–97.3%.

$^1$H NMR (DMSO-d6): [ppm]=8.25–8.22 (m, 2 H), 8.16–8.12 (m, 1 H), 7.95–7.93 (m, 2 H), 7.86–7.74 (m, 4 H), 7.52–7.45 (m, 3 H), 7.21–7.17 (m, 2 H), 7.16–7.11 (m, 1 H), 6.89–6.78 (m, 3 H), 6.75–6.53 (m, 4 H).

EXAMPLE 4 fac-Tris[2-(2-pyridinyl-κN)(5-bromophenyl)-κC]iridium(III)

7.120 g (40 mmol) of N-bromosuccinimide were added with the exclusion of light to an efficiently stirred solution of 6.548 g (10.0 mmol) of fac-tris[2-(2-pyridinyl-κN)phenyl-κC]iridium(III) in 1500 ml of dichloromethane. After approx. 1 h, the product precipitated out of the yellow reaction solution as a yellow, microcrystalline precipitate. The suspension was stirred at room temperature for a further 20 h. After concentrating the suspension under reduced pressure to a volume of 200 ml, the microcrystalline precipitate was filtered off (P4), washed ten times with 100 ml of water and once with 100 ml of ethanol, and subsequently dried under reduced pressure (60° C., $10^{-4}$ mbar). The yield, at a purity of >99.7% by $^1$H NMR, was 8.520–8.610 g, corresponding to 95.5–96.5%.

$^1$H NMR (DMSO)=d6): [ppm]=8.26 (br. dd. 1 H, $^3J_{HH}$=8.4 Hz, $^4J_{HH}$=1.3 Hz, H6), 7.96 (d, 1 H, $^4J_{HH}$=2.0 Hz, H6'), 7.85 (ddd, 1 H, $^3J_{HH}$=8.4 Hz, $^3J_{HH}$=8.4 Hz, $^4J_{HH}$=1.6 Hz, H5), 7.49 (dd, 1 H, $^3J_{HH}$=5.4 Hz, $^4J_{HH}$=1.6 Hz, H3), 7.20 (ddd, 1 H, $^3J_{HH}$=8.4 Hz, $^3J_{HH}$=5.4 Hz, $^4J_{HH}$=1.3 Hz, H4), 6.89 (dd, 1 H, $^3J_{HH}$=8.0 Hz, $^4J_{HH}$=2.0 Hz, H4'), 6.53 (d, 1 H, $^3J_{HH}$=8.0 Hz, H3'). $^{13}$C{$^1$H} NMR (DMSO-d6): [ppm]= 163.8 (q), 158.1 (q), 147.2 (t), 146.8 (q), 138.0 (t), 137.6 (t), 131.8 (t), 126.7 (t), 123.9 (t), 120.0 (t), 113.5 (q).

EXAMPLE 5 fac-Tris[2-(2-pyridinyl-κN)(5-bromophenyl)-κC]iridium(III)

With the exclusion of light, 12.925 g=17.42 ml (100 mmol) of N-ethyl-diisopropylamine, 7.991 g=2.58 ml (50 mmol) of bromine and 16.2 mg (0.1 mmol) of anhydrous iron(III) chloride were added to an efficiently stirred solution of 6.548 g (10.0 mmol) of fac-tris[2-(2-pyridinyl-κN)phenyl-κC]iridium(III) in 1500 ml of dichloromethane. After approx. 6 h, the product precipitated out of the red-brown reaction solution as a yellow, microcrystalline precipitate. The suspension was stirred at room temperature for a further 16 h. After concentrating the suspension under reduced pressure to a volume of 200 ml, the microcrystalline precipitate was filtered off with suction (P4), washed ten times with 100 ml of water and three times 100 ml of ethanol, and subsequently dried under reduced pressure (60° C., $10^{-4}$ mbar). The yield, at a purity of >99.5% by $^1$H NMR, was 8.340–8.481 g, corresponding to 93.6–95.1%.

$^1$H NMR and $^{13}$C{$^1$H} NMR spectroscopy data, see example 4.

EXAMPLE 6 fac-Tris[2-(2-pyridinyl-κN)(5-iodophenyl)-κC]iridium(III)

With the exclusion of light, 10.152 g (40 mmol) of iodine and 6.442 g (20 mmol) of iodobenzene diacetate were added to an efficiently stirred solution of 6.548 g (10.0 mmol) of fac-tris[2-(2-pyridinyl-κN)phenyl-κC]iridium(III) in 1500 ml of dichloromethane. After approx. 24 h, the product precipitated out of the red-brown reaction solution as a yellow, microcrystalline precipitate. The suspension was stirred at room temperature for a further 16 h. After concentrating the suspension under reduced pressure to a volume of 100 ml, it was admixed with 500 ml of ethanol, and the microcrystalline precipitate was subsequently filtered off (P4), washed three times with 100 ml of ethanol, three times with 100 ml of water and three times with 100 ml of ethanol, and dried under reduced pressure (60° C., $10^{-4}$ mbar). The yield, at a purity of 99.7% by $^1$H NMR, was 9.819–9.995 g, corresponding to 95.1–96.8%.

$^1$H NMR (DMSO-d6): [ppm]=8.22 (br. D, 1 H, $^3J_{HH}$=8.4 Hz, H6), 8.06 (d, 1 H, $^4J_{HH}$=2.0 Hz, H6'), 7.83 (br. m, 1 H, H5), 7.45 (br. d, 1 H, $^3J_{HH}$=5.4 Hz, H3), 7.40 (br. m, 1 H, H4), 7.02 (dd, 1 H, $^3J_{HH}$=8.0 Hz, $^4J_{HH}$=2.0 Hz, H4'), 6.41 (d, 1 H, $^3J_{HH}$=8.0 Hz, H3').

EXAMPLE 7 fac-Tris[2-(2-pyridinyl-κN)(5-iodophenyl)-κC]iridium(III)

With the exclusion of light, 13.500 g (60 mmol) of N-iodosuccinimide and 16 mg (0.1 mmol) of iron(III) chloride were added to an efficiently stirred solution of 6.548 g (10.0 mmol) of fac-tris[2-(2-pyridinyl-κN)phenyl-κC]iridium(III) in 1500 ml of dichloromethane. After approx. 48 h, the product precipitated out of the yellow reaction solution as a yellow, microcrystalline precipitate. The suspension was stirred at room temperature for a further 16 h. After concentrating the suspension under reduced pressure to a volume of 100 ml, it was admixed with 500 ml of ethanol, and the microcrystalline precipitate was subsequently filtered off (P4), washed three times with 100 ml of ethanol, three times with 100 ml of water and three times with 100 ml of ethanol, and dried under reduced pressure (60° C., $10^{-4}$ mbar). The yield, at a purity of >99.5% by $^1$H NMR, was 9.427–9.657 g, corresponding to 91.3–93.5%.

$^1$H NMR NMR spectroscopy data, see example 6.

EXAMPLE 8 fac-Tris[2-(2-pyridinyl-κN)-5-bromo-4-fluorophenyl-κC]iridium(III)

With the exclusion of light, a solution of 5.323 g (30.2 mmol) of N-bromosuccinimide (content of active bromine, 98%) in 100 ml dichloromethane was added dropwise over 1 h to an efficiently stirred solution of 7.082 g (10.0 mmol) of fac-tris[2-(2-pyridinyl-κN)4-fluorophenyl-κC]iridium (III) in 1200 ml of dichloromethane. The solution was stirred at room temperature for a further 15 h. After concentrating under reduced pressure to a volume of 100 ml, the solution was admixed with 500 ml of ethanol. Subsequently, the microcrystalline precipitate was filtered off (P4), washed three times with 50 ml of ethanol and then dried under reduced pressure (60° C., $10^{-4}$ mbar). The yield, at a purity of >99.7% by $^1$H-NMR, was 8.916 g, corresponding to 94.3%.

$^1$H NMR (DMSO-d6): [ppm]=8.29 (d, 1 H, $^3J_{HH}$=8.0 Hz, H6), 8.18 (d, 1 H, $^4J_{HF}$=6.7 Hz, H6'), 7.89 (br. dd, 1 H, $^3J_{HH}$=8.0 Hz, $^3J_{HH}$=6.0 Hz, H5), 7.48 (d, 1H, $^3J_{HH}$=6.0 Hz, H3), 7.23 (br. dd, 1H, $^3J_{HH}$=6.0 Hz, $^3J_{HH}$=6.0 Hz, H4), 6.27 (d, 1H, $^3J_{HF}$=9.7 Hz, H3').

EXAMPLE 9 fac-Tris[2-(2-pyridinyl-κN)-5-bromo-4-methoxyphenyl-κC]iridium(III)

7.120 g (40.0 mmol) of N-bromosuccinimide were added with the exclusion of light to an efficiently stirred solution of 7.449 g (10.0 mmol) of fac-tris[2-(2-pyridinyl-κN)-4-methoxyphenyl-κC]iridium(III) in 1500 ml of dichloromethane. The solution was stirred at room temperature for a further 20 h. After adding 0.3 ml of hydrazine hydrate and concentrating the suspension under reduced pressure to a volume of 200 ml, it was admixed with 500 ml of ethanol and stirred at room temperature for 20 h. The precipitated microcrystalline solid was filtered off (P4), washed ten times with 100 ml of water/ethanol (1:1 vv) and washed once with 100 ml of ethanol, and subsequently dried under reduced pressure (60° C., $10^{-4}$ mbar). The yield, at a purity of >99.7% by $^1$H NMR, was 9.190 g, corresponding to 93.6%.

$^1$H NMR (DMSO-d6): [ppm]=8.11 (d, 1 H, $^3J_{HH}$=7.8 Hz, H6), 7.96 (s, 1 H, H6'), 7.78 (br. dd, 1 H, $^3J_{HH}$=7.8 Hz, $^3J_{HH}$=6.0 Hz, H5), 7.48 (d, 1H, $^3J_{HH}$=6.0 Hz, H3), 7.21 (br. dd, 1H, $^3J_{HH}$=6.0 Hz, $^3J_{HH}$=6.0 Hz, H4), 6.35 (s, 1H, H3').

EXAMPLE 10

Tetrakis[(2-pyridinyl-κN)-5-bromophenyl)-κC][di-μ-chloro]diiridium(III)

With the exclusion of light, a solution of 10.680 g (60 mmol) of N-bromosuccinimide (content of active bromine: 98%) was added to an efficiently stirred solution of 10.721 g (10.0 mmol) of tetrakis[(2-pyridinyl-κN)phenyl-κC][di-μ-chloro]diiridium(III) and 1.081 g (10 mmol) of hydroquinone in 1200 ml of dichloromethane. The solution was stirred at room temperature for a further 15 h. After concentrating under reduced pressure to a volume of 200 ml, the solution was admixed with 2000 ml of ethanol. Subsequently, the microcrystalline precipitate was filtered off (P4), washed three times with 50 ml of ethanol and then dried under reduced pressure (60° C., $10^{-4}$ mbar). The yield, at a purity of >99.0% by $^1$H NMR, was 12.68 g, corresponding to 91.0%.

$^1$H NMR (CDCl$_3$): [ppm]=9.11 (d, 1 H, $^3J_{HH}$=5.7 Hz, H6), 7.79 (d, 1 H, $^3J_{HH}$=7.6 Hz, H3), 7.72 (br. dd, 1 H, H5), 7.54 (d, 1H, $^4J_{HH}$=2.15 Hz, H6'), 6.74 (br. dd, 1H, H4), 6.62 (dd, 1H, $^4J_{HH}$=2.15 Hz, $^3J_{HH}$=8.35 Hz, H4'), 5.65 (d, 1H, $^3J_{HH}$=8.35 Hz, H3').

What is claimed is:

1. A compound of the formula (I) or (II)

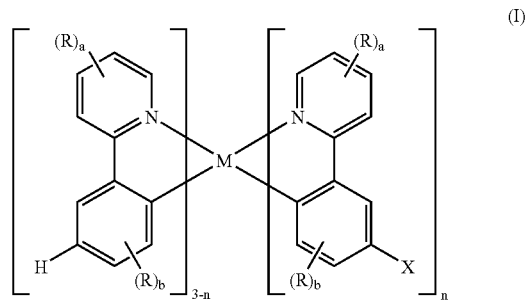

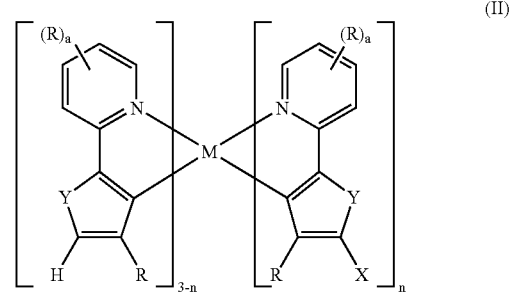

wherein

M is Rh or Ir,

X is the same or different and is F, Cl, Br or I,

Y is the same or different and is O, S or Se,

R is the same or different at each occurrence and is H, F, Cl, Br, NO$_2$, CN, a straight-chain or branched or cyclic alkyl or alkoxy group which has from 1 to 20 carbon atoms and in which one or more nonadjacent CH$_2$ groups is optionally replaced by —O—, —S—, —NR$^1$— or —CONR$^2$— and in which one or more hydrogen atoms in said alkoxy group is optionally replaced by F, or an aryl or heteroaryl group having from 4 to 14 carbon atoms which is optionally substituted by one or more nonaromatic R radicals; and a plurality of R substituents, either on the same ring or on the two different rings together in the same ligand in turn optionally encompasses a further monocyclic carbon ring system;

R$^1$ and R$^2$ are the same or different and are each H or an aliphatic or aromatic hydrocarbon radical having 1 to 20 carbon atoms, a is the same or different and is 0, 1, 2, 3 or 4, b is the same or different and is 0, 1, 2 or 3, and n is 1, 2 or 3.

2. The compound as claimed in claim 1, wherein
a is 0, 1 or 2 and
b is 0 or 1.

3. A compound of the formula (Ia) or (IIa)

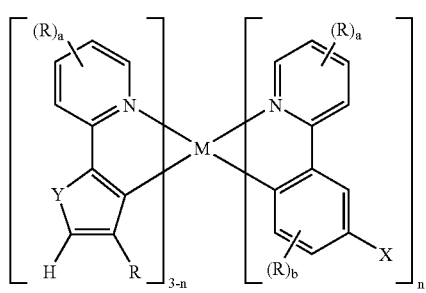
(Ia)

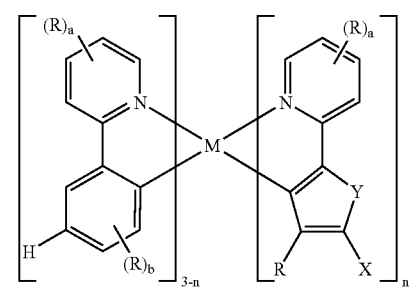
(IIa)

wherein
M is Rh or Ir,
X is the same or different and is F, Cl, Br or I,
Y is the same or different and is O, S or Se,
R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NP^1$— or —$CONR^2$— and in which one or more hydrogen atoms in said alkoxy group is optionally replaced by F, or an aryl or heteroaryl group having from 4 to 14 carbon atoms which is optionally substituted by one or more nonaromatic R radicals;
and a plurality of R substituents, either on the same ring or on the two different rings together in the same ligand in turn optionally encompasses a further monocyclic carbon ring system;
$R^1$ and $R^2$ are the same or different and are each H or an aliphatic or aromatic hydrocarbon radical having 1 to 20 carbon atoms,
a is the same or different and is 0, 1, 2, 3 or 4,
b is the same or different and is 0, 1, 2 or 3, and
n is 1, 2 or 3.

4. The compound as claimed in claim 3, wherein
a is 0, 1 or 2 and
b is 0 or 1.

5. A compound of the formula (V) or (VII)

Compounds (V)

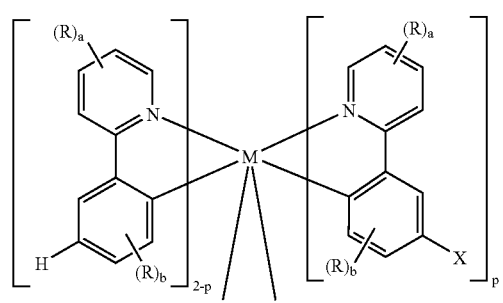

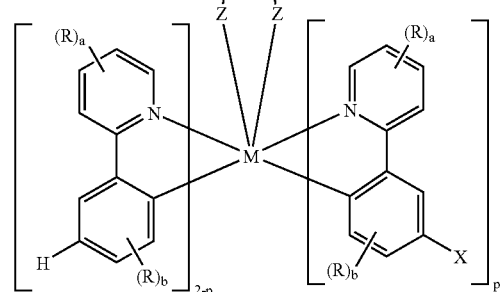

Compounds (VII)

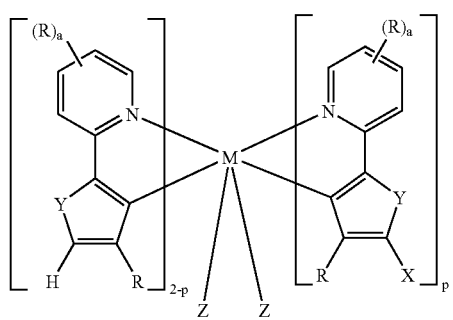

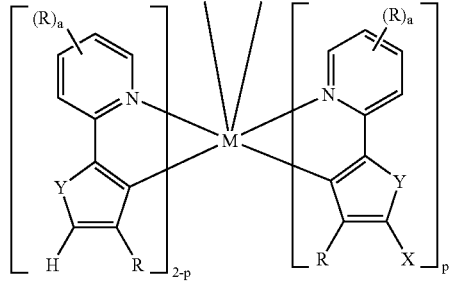

wherein
M is Rh or Ir,
X is F, Cl, Br or I,
Y is O, S or Se,
Z is F, Cl, Br, I, O—$R^1$, S—$R^1$ or $N(R^1)_2$,
R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NR^1$— or —$CONR^2$— and in which one or more hydrogen atoms in said alkoxy group is optionally replaced by F, or an aryl or heteroaryl group having from 4 to 14 carbon atoms which is optionally substituted by one or more nonaromatic R radicals; and a plurality of R substituents, either on the same ring or on the two different rings in the same ligand together in turn optionally encompasses a further monocyclic carbon ring system;

$R^1$ and $R^2$ are the same or different and are each H or an aliphatic or aromatic hydrocarbon radical having 1 to 20 carbon atoms, a is 0, 1, 2, 3 or 4, b is 0, 1, 2 or 3, and p is 1 or 2.

6. The compound claimed in claim 5, wherein a is 0, 1 or 2 and b is 0 or 1.

7. A compound of the formula (IX), (XI), (XIII) or (XV)

Compounds (IX)

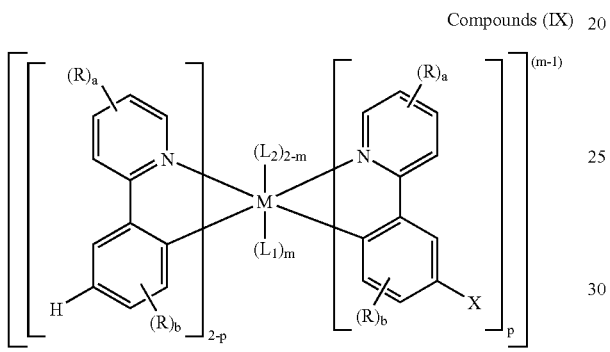

Compounds (XI)

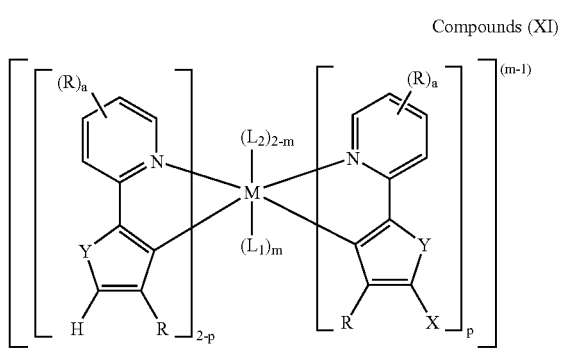

Compounds (XIII)

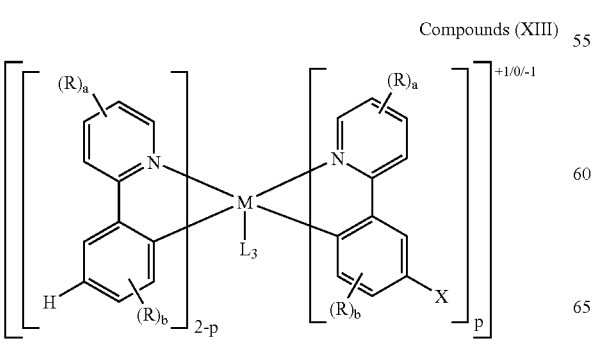

-continued

Compounds (XV)

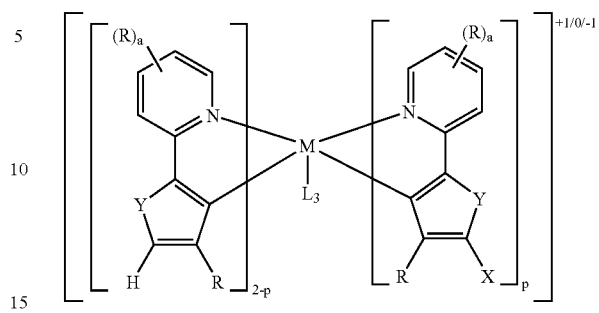

wherein

M is Rh or Ir,

X is F, Cl, Br or I,

Y is O, S or Se,

R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NR^1$— or —$CONR^2$— and in which one or more hydrogen atoms in said alkoxy group is optionally replaced by F, or an aryl or heteroaryl group having from 4 to 14 carbon atoms which is optionally substituted by one or more nonaromatic R radicals; and a plurality of R substituents, either on the same ring or on the two different rings in the same ligand together in turn optionally encompasses a further monocyclic carbon ring system;

$R^1$ and $R^2$ are the same or different and are each H or an aliphatic or aromatic hydrocarbon radical having 1 to 20 carbon atoms, $L_1$ is a neutral, monodentate ligand, $L_2$ is a monoanionic, monodentate ligand, $L_3$ is a neutral or mono- or dianionic bidentate ligand, a is 0, 1, 2, 3 or 4, b is 0, 1, 2, or 3, m is 0, 1 or 2, and p is 1 or 2.

8. The compound as claimed in claim 7, wherein a is 0, 1 or 2 and b is 0 or 1.

9. The compound as claimed in claim 7, wherein $L_1$ is carbon monoxide, an isonitrile, an amine, morpholine, a phosphine, a phosphite, an arsine, a stibine, or a nitrogen heterocycle.

10. The compound as claimed in claim 9, wherein $L_1$ is tert-butylisonitrile, cyclohexylisonitrile, adamantylisonitrile, trimethylamine, triethylamine, trifluorophosphine, trimethylphosphine, tricyclohexylphosphine, tri-tert-butylphosphine, triphenylphosphine, tris(pentafluorophenyl) phosphine, trimethyl phosphite, triethyl phosphite, trifluoroarsine, trimethylarsine, tricyclohexylarsine, tri-tert-butylarsine, triphenylarsinine, tris(pentafluorophenyl)arsine, trifluorostibine, trimethylstibine, tricyclohexylstibine, tri-tert-butylstibine, triphenylstibine, tris(pentafluorophenyl)stibine pyridine, pyridazine, pyrazine or triazine.

11. The compound as claimed in claim 7, wherein $L_2$ is a halide, cyanide, cyanate, isocyanate, thiocyanate, isothiocyanate, an alkoxide, a thioalkoxide, an amid, pyrrolide, morpholide, a carboxylate or an anionic nitrogen heterocycle.

12. The compound as claimed in claim 10, wherein $L_2$ is methoxide, ethoxide, propoxide, iso-propoxide, tert-butoxide, phenoxide, methanethiolate, ethanethiolate, propanethiolate, iso-propanethiolate, tert-thiobutoxide, thiophenoxide, dimethylamide, diethylamide, di-iso-propylamide, acetate, trifluoroacetate, propionate, benzoate, pyrrolide, imidazolide or pyrazolide.

13. The compound as claimed in claim 7, wherein $L_3$ is a diamine, an amine, a diimine, a heterocycle containing two nitrogen atoms, o-phenanthroline, a diphosphine, a 1,3-diketonate derived from 1,3-diketone, a 3-ketonate derived from 3-keto esters, a carboxylate derived from amino carboxylic acids, glycine, dimethylglycine, alanine, dimethylaminoalanine, a salicyliminate derived from salicylimine, a dialkoxide derived from dialcohols or a ditholate derived from dithiols.

14. The compound as claimed in claim 12, wherein $L_3$ is ethylenediamine N,N,N', N'-tetramethylethylenediamine, propylenediamine, N,N,N,',N'-tetramethylpropylenediamine, cis-, trans-diaminocyclohexane, cis-, trans- N,N,N', N'-tetramethyldiaminocyclohexane, 2[(1-(phenylimino)ethyl]pyridine, 2[(I-(2-methylphenylimino)-ethyl]pyridine, 2[(1-(2,6-di-iso-propylphenylimino)ethyl]pyridine, 2[(1-(methylimino)ethyl]pyridine, 2[(1-(ethylimino)ethyl]pyridine, 2[(1-(iso-propylimino)ethyl]pyridine, 2[(1-(tert-butylimino)ethyl]pyridine, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane 1,2-(phenylimino)ethane, 1,2-bis(2-ethanemethylphenylimino)ethane, I2-bis(2,6di-iso-propylphenylimino, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, 2,2'-bipyridine, bis(diphenylphosphino)methane, bis(diphenylphosphino)ethane, bis(diphenylphosphino)propane, bis(dimethylphosphino)methane, bis(dimethylphosphino)ethane, bis(dimethylphosphino)propane, bis(diethyl phosphino)methane, bis(diethylphosphino)ethane, bis(diethylphosphino)propane, bis(di-tert-buthylphosphino)methane, bis(di-tert-butylphosphino)ethane, bis(tert-butylphosphino)propane, acetylacetone, benzoylacetone, I 5-diphenylacetylacetone, dibenzoylmethane, bis(1,1,1-trifluoroacetyl)methane, ethyl acetoacetate, pyridine-2-carboxylic acid, quinoline-2-carboxylic acid, methylsalicylimine, ethylsalicylimine, phenylsalicylimine, ethylene glycol, 1,3-propylene glycol 1,2-ethylenedithiolate or 1,3-propylenedithiolate.

15. A process for preparing the compounds defined in claim 1, which comprises reacting the compounds (III) or (IV)

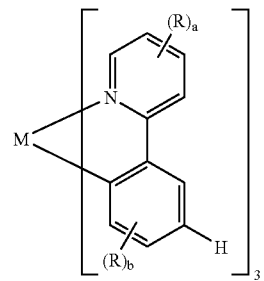

Compounds (III)

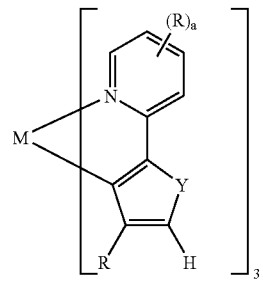

Compounds (IV)

wherein M and the radicals and indices Y, R, a and b are as defined in claim 1 with halogenating agents.

16. A process for preparing the compounds defined in claim 5, which comprises reacting the compounds (VI) or (VIII)

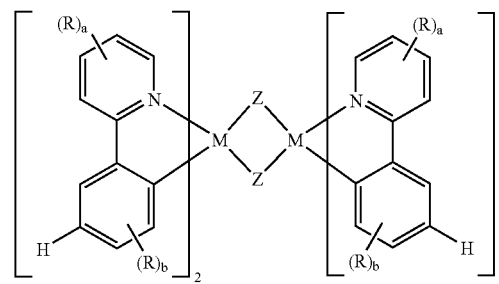

Compounds (VI)

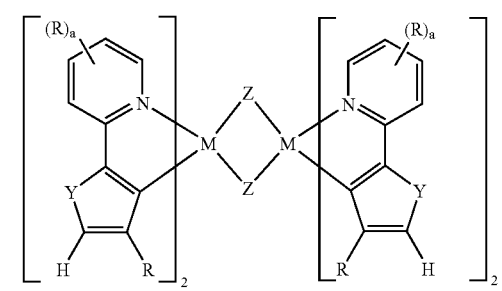

Compounds (VIII)

wherein M and the radicals and indices Z, Y, R, a and b are as defined in claim 5 with halogenating agents.

17. A process for preparing the compounds defined in claim 7, which comprises reacting the compounds (X), (XII), (XIV) or (XVI)

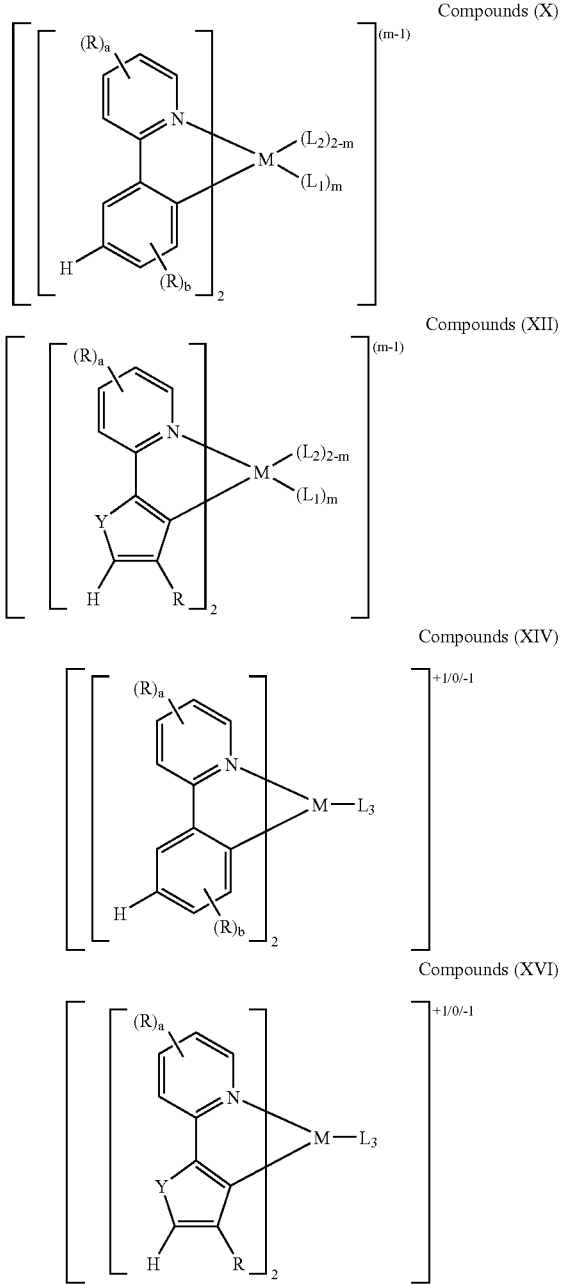

wherein M and the radicals and indices $L_1$, $L_{2, L3}$, Y, R, a, b and m are as defined above in claim 7 with halogenating agents.

18. The process as claimed in claim 15, wherein the halogenating agent used is a halogen $X_2$ or an interhalogen X—X and a base in a ratio of from 1:1 to 1:100, or an organic bromine complex, and in each case optionally a Lewis acid in a ratio (halogen to Lewis acid) of from 1:0.1 to 1:0.0001.

19. The process as claimed in claim 16, wherein the halogenating agent used is a halogen $X_2$ or an interhalogen X—X and a base in a ratio of from 1:1 to 1:100, or an organic bromine complex, and in each case optionally a Lewis acid in a ratio (halogen to Lewis acid) of from 1:0,1 to 1:0.0001.

20. The process as claimed in claim 17, wherein the halogenating agent used is a halogen $X_2$ or an interhalogen X—X and a base in a ratio of from 1:1 to 1:100, or an organic bromine complex, and in each case optionally a Lewis acid in a ratio (halogen to Lewis acid) of from 1:0,1 to 1:0,0001.

21. The process as claimed in claim 18, wherein the halogen or interhalogen used is chlorine, bromine, iodine, chlorine fluoride, bromine fluoride, iodine fluoride, bromine chloride, iodine chloride or iodine bromide respectively and the organic bromine complex is pyridinium perbromide.

22. The process as claimed in claim 19, wherein the halogen or interhalogen used is chlorine, bromine, iodine, chlorine fluoride, bromine fluoride, iodine fluoride, bromine chloride, iodine chloride or iodine bromide respectively and the organic bromine complex is pyridinium perbromide.

23. The process as claimed in claim 20, wherein the halogen or interhalogen used is chlorine, bromine, iodine, chlorine fluoride, bromine fluoride, iodine fluoride, bromine chloride, iodine chloride or iodine bromide respectively and the organic bromine complex is pyridinium perbromide.

24. The process as claimed in claim 18, wherein the base used is an organic amine or salts of carboxylic acids or inorganic bases.

25. The process as claimed in claim 19, wherein the base used is an organic amine or salts of carboxylic acids or inorganic bases.

26. The process as claimed in claim 20, wherein the base used is an organic amine or salts of carboxylic acids or inorganic bases.

27. The process as claimed in claim 24, wherein the base used is triethylamine, tri-n-butylamine, diisopropylethylamine, morpholine, N-methylmorpholine, pyridine, sodium acetate, sodium propionate, sodium benzoate, sodium or potassium phosphate or hydrogenphosphate, sodium or potassium hydrogencarbonate, sodium or potassium carbonate.

28. The process as claimed in claim 25, wherein the base used is triethylamine, tri-n-butylamine, diisopropylethylamine, morpholine, N-methylmorpholine, pyridine, sodium acetate, sodium propionate, sodium benzoate, sodium or potassium phosphate or hydrogenphosphate, sodium or potassium hydrogencarbonate, sodium or potassium carbonate.

29. The process as claimed in claim 26, wherein the base used is triethylamine, tri-n-butylamine, diisopropylethylamine, morpholine, N-methylmorpholine, pyridine, sodium acetate, sodium propionate, sodium benzoate, sodium or potassium phosphate or hydrogenphosphate, sodium or potassium hydrogencarbonate, sodium or potassium carbonate.

30. The process as claimed in claim 18, wherein said Lewis acid is used and is selected from the group consisting of boron trifluoride, boron trifluoride etherate, boron trichloride, boron tribromide, boron triiodide, aluminum trichloride, aluminum tribromide, aluminum triiodide, iron(III) chloride, iron(III) bromide, zinc(II) chloride, zinc(II) bromide, tin(IV) chloride, tin (IV) bromide, phosphorus pentachloride, arsenic pentachloride and antimony pentachloride.

31. The process as claimed in claim 19, wherein said Lewis acid is used and is selected from the group consisting of boron trifluoride, boron trifluoride etherate, boron trichloride, boron tribromide, boron triiodide, aluminum trichloride, aluminum tribromide, aluminum triiodide, iron(III) chloride, iron(III) bromide, zinc(II) chloride, zinc(II) bromide, tin(IV) chloride, tin(IV)bromide, phosphorus pentachloride, arsenic pentachloride and antimony pentachloride.

32. The process as claimed in claim 20, wherein said Lewis acid is used and is selected from the group consisting of boron trifluoride, boron trifluoride etherate, boron trichloride, boron tribromide, boron triiodide, aluminum trichloride, aluminum tribromide, aluminum triiodide, iron(III) chloride, iron (III)bromide, zinc(II) chloride, zinc(II) bromide, tin (IV) chloride, tin(IV)bromide, phosphorus pentachloride, arsenic pentachloride and antimony pentachloride.

33. The process as claimed in claim 15, wherein the halogenating agent used is an organic N—X compound.

34. The process as claimed in claim 16, wherein the halogenating agent used is an organic N—X compound.

35. The process as claimed in claim 17, wherein the halogenating agent used is an organic N—X compound.

36. The process as claimed in claim 33, wherein the organic N—X compound is 1-(chloromethyl)-4-fluoro-1,4-diazoniabicyclo[2.2.2]-octane bis(tetrafluoroborate), N-halocarboxamide, N-halocarboximide N-dihalosulfonamide or N-halosulfonamide salts.

37. The process as claimed in claim 34, wherein the organic N—X compound is 1-(chloromethyl)-4-fluoro,1,4-diazoniabicyclo[2.2.2]-octane bis(tetrafluoroborate), N-halocarboxamide, N-halocarboximide, N-dihalosulfonamide or N-halosulfonamide salts.

38. The process as claimed in claim 35, wherein the organic N—X compound is 1-(chloromethyl)-4-fluoro-1,4-diazoniabicyclo[2.2.2]-octane bis(tetrafluoroborate), N-halocarboxamide, N-halocarboximide, N-dihalosulfonamide or N-halosulfonamide salts.

39. The process as claimed in claim 15, wherein the halogenating agent used is an organic O—X compound and halogens $X_2$ in a molar ratio of from 0.5:1 to 1:1.

40. The process as claimed in claim 16, wherein the halogenating agent used is an organic O—X compound and halogens $X_2$ in a molar ratio of from 0.5:1 to 1:1.

41. The process as claimed in claim 17, wherein the halogenating agent used is an organic O—X compound and halogens $X_2$ in a molar ratio of from 0.5:1 to 1:1.

42. The process as claimed in claim 39, wherein the organic O—X compound used is iodoaryl dicarboxylate.

43. The process as claimed in claim 40, wherein the organic O—X compound used is iodoaryl dicarboxylate.

44. The process as claimed in claim 41, wherein the organic O—X compound used is iodoaryl dicarboxylate.

45. The process as claimed in claim 42, wherein said iodoaryl dicarboxylate is iodobenzene diacetate or bistrifluoroacetoxyiodobenzene.

46. The process as claimed in claim 43, wherein said iodoaryl dicarboxylate is iodobenzene diacetate or bistrifluoroacetoxyiodobenzene.

47. The process as claimed in claim 44, wherein said iodoaryl dicarboxylate is iodobenzene diacetate or bistrifluoroacetoxyiodobenzene.

48. The process as claimed in claim 18, wherein a stoichiometric ratio of the halogenating agents based on the content of active halogen, to the compounds (III) or (IV) of 1:1 is used.

49. The process as claimed in claim 19, wherein a stoichiometric ratio of the halogenating agents based on the content of active halogen, to the compounds (VI) or (VIII) of 1:1 is used.

50. The process as claimed in claim 20, wherein a stoichiometric ratio of the halogenating agents based on the content of active halogen, to the compounds (X), (XII), (XIV) or (XVI) of 1:1 is used.

51. The process as claimed in claim 33, wherein a stoichiometric ratio of the halogenating agents based on the content of active halogen, to the compounds (III) or (IV) of 1:1 is used.

52. The process as claimed in claim 34, wherein a stoichiometric ratio of the halogenating agents based on the content of active halogen, to the compounds (VI) or (VIII) of 1:1 is used.

53. The process as claimed in claim 35, wherein a stoichiometric ratio of the halogenating agents based on the content of active halogen, to the compounds (X), (XII), (XIV) or (XVI) of 1:1 is used.

54. The process as claimed in claim 39, wherein a stoichiometric ratio of the halogenating agents based on the content of active halogen, to the compounds (III) or (IV) 1:1 is used.

55. The process as claimed in claim 40, wherein a stoichiometric ratio of the halogenating agents based on the content of active halogen, to the compounds (VI) or (VIII) of 1:1 is used.

56. The process as claimed in claim 41, wherein a stoichiometric ratio of the halogenating agents based on the content of active halogen, to the compounds (X), (XII), (XIV) or (XVI) of 1:1 is used.

57. The process as claimed in claim 18, wherein a stoichiometric ratio of the halogenating agents based ante content of active halogen, to the compounds (III) or (IV) of 2:1 is is used.

58. The process as claimed in claim 19, wherein a stoichiometric ratio of the halogenating agents based on the content of active halogen, to the compounds (VI) or (VIII) of 2:1 is used.

59. The process as claimed in claim 20, wherein a stoichiometric ratio of the halogenating agents based on the content of active halogen, to the compounds (X), (XII), (XIV) or (XVI) of 2:1 is used.

60. The process as claimed in claim 33, wherein a stoichiometric ratio of the halogenating agents based on the content of active halogen, to the compounds (III) or (IV) of 2:1 of is used.

61. The process as claimed in claim 34, wherein a stoichiometric ratio of the halogenating agents based on the content of active halogen, to the compounds (VI) or (VIII) of 2:1 is used.

62. The process as claimed in claim 35, wherein a stoichiometric ratio of the halogenating agents based on the content of active halogen, to the compounds (X), (XII), (XIV) or (XVI) of 2:1 is used.

63. The process as claimed in claim 39, wherein a stoichiometric ratio of the halogenating agents based on the content of active halogen, to the compounds (III) or (IV) of 2:1 is used.

64. The process as claimed in claim 40, wherein a stoichiometric ratio of the halogenating agents based on the content of active halogen, to the compounds (VI) or (VIII) of 2:1 is used.

65. The process as claimed in claim 41, wherein a stoichiometric ratio of the halogenating agents based on the content of active halogen, to the compounds (X), (XII), (XIV) or (XVI) of 2:1 is used.

66. The process as claimed in claim 18, wherein a stoichiometric ratio of the halogenating agents based on the content of active halogen, to the compounds (III) or (IV) of 3:1 is used.

67. The process as claimed in claim 33, wherein a stoichiometric ratio of the halogenating agents based on the content of active halogen, to compounds (III) or (IV) of 3:1 is used.

68. The process as claimed in claim 39, wherein a stoichiometric ratio of the halogenating agents based on the content of active halogen, to compounds (III) or (IV) of 3:1 is used.

69. The process as claimed in claim 33, wherein the organic N—X compound is N-chloroacetamide, N-bromoacetamide, N-iodoacetamide, N-chloropropionamide N-bromopropionamide, N-iodopropionamide, N-chlorobenzamide, N-bromobenzamide, N-iodobenzamide, N-chlorosuccinimide, N-bromosuccinimide, N-iodosuccinimide, N-chlorophthalimide, N-bromophthalimide, N-iodophthalimide, benzenesulfo-N-dibromamide, chloramine B or chloramine T.

70. The process as claimed in claim 34, wherein the organic N—X compound is N-chloroacetamide, N-bromoacetamide, N-iodoacetamide, N-chloropropionamide, N-bromopropionamide, N-iodopropionamide, N-chlorobenzamide, N-bromobenzamide, N-iodobenzamide, N-chlorosuccinimide, N-bromosuccinimide, N-iodosuccinimide, N-chlorophthalimide, N-bromophthalimide, N-iodophthalimide, benzenesulfo-N-dibromamide, chloramine B or chloramine T.

71. The process as claimed in claim 35, wherein the organic N—X compound is N-chloroacetamide, N-bromoacetamide, N-iodoacetamide, N-chloropropionamide, N-bromopropionamide, N-iodopropionamide, N-chlorobenzamide, N-bromobenzamide, N-iodobenzamide, N-chlorosuccinimide, N-bromosuccinimide, N-iodosuccinimide, N-chlorophthalimide, N-bromophthalimide, N-iodophthalimide, benzenesulfo-N-dibromamide, chloramine B or chloramine T.

72. The process as claimed in claim 19, wherein a stoichiometric ratio of the halogenating agents based on the content of active halogen, to the compounds (VI) or (VIII) in the range from 4:1 to 1000:1 is used.

73. The process as claimed in claim 34, wherein a stoichiometric ratio of the halogenating agents based on the content of active halogen, to the compounds (VI) or (VIII) in the range from 4:1 to 1000:1 is used.

74. The process as claimed in claim 40, wherein a stoichiometric ratio of the halogenating agents based on the content of active halogen, to the compounds (VI) or (VIII) in the range from 4:1 to 1000:1 is used.

75. The compound as claimed in claim 1, wherein the compound has a purity (determined by means of 1H NMR or HPLC) of more than 99%.

76. The compound as claimed in claim 3, wherein the compound has a purity (determined by means of 1H NMR or HPLC) of more than 99%.

77. The compound as claimed in claim 5, wherein the compound has a purity (determined by means of 1H NMR or HPLC) of more than 99%.

78. A conjugated or semiconjugated polymer containing one or more compounds of the formula (I) and/or (II)

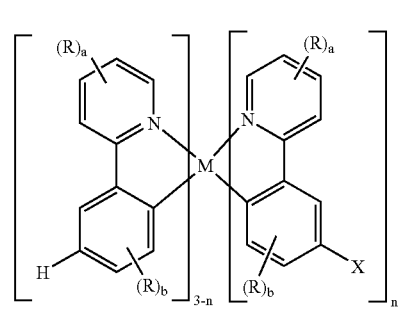

Compounds (I)

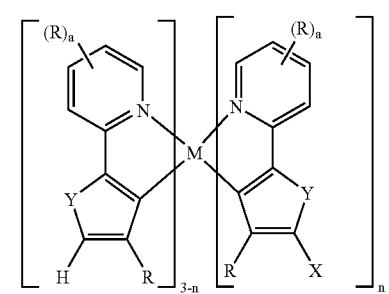

Compounds (II)

and/or of the formula (Ia) and/or (IIa)

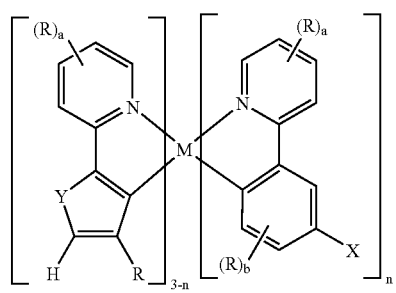

Compounds (Ia)

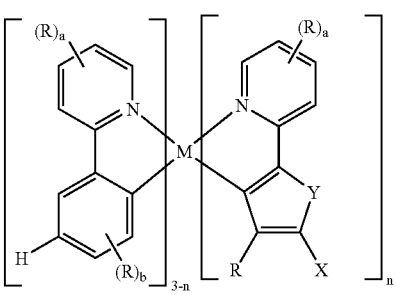

Compounds (IIa)

and/or of the formula (IX), (XI), (XIII) and/or (XV)

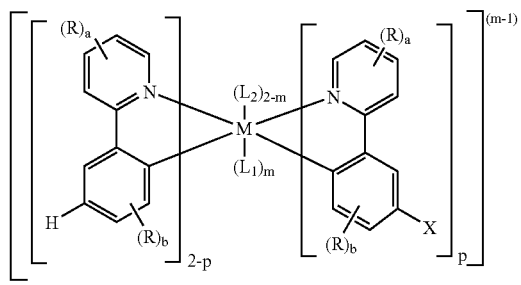

Compounds (IX)

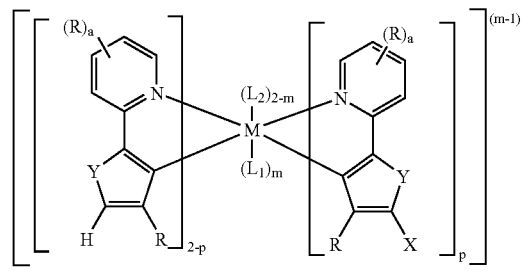

Compounds (XI)

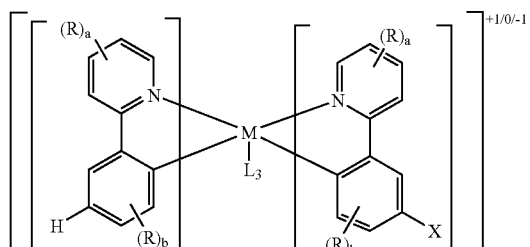

Compounds (XIII)

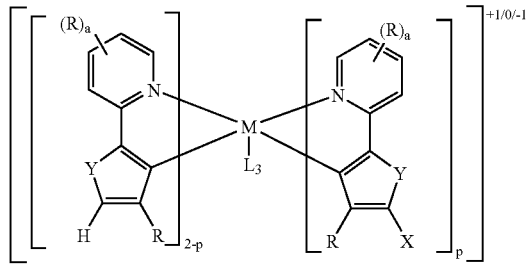

Compounds (XV)

where the symbols and indices are defined as follows:

M is Rh or Ir,

Y is the same or different and is O, S or Se,

R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NR^1$— or —$CONR^2$— and in which one or more hydrogen atoms in said alkoxy group is optionally replaced by F, or an aryl or heteroaryl group having from 4 to 14 carbon atoms which is optionally substituted by one or more nonaromatic R radicals; and a plurality of R substituents, either on the same ring or on the two different rings together in the same ligand in turn optionally encompasses a further monocyclic carbon ring system;

$R^{1\ and\ R2}$ are the same or different and are H or an aliphatic or aromatic hydrocarbon radical having 1 to 20 carbon atoms, $L_1$ is a neutral, monodentate ligand, $L_2$ is a monoanionic, monodentate ligand, $L_3$ is a neutral or mono- or dianionic bidentate ligand, a is the same or different and is 0, 1, 2, 3 or 4, b is the same or different and is 0, 1, 2 or 3, n is 1, 2 or 3, m is 0, 1 or 2, p is 1 or 2, and X is a bond to the conjugated or semiconjugated polymer.

79. The polymer as claimed in claim 78, wherein the polymer is selected from the group consisting of polyfluorenes, poly-spiro-bifluorenes, poly-para-phenylenes, polycarbazoles and polythiophenes.

80. The polymer as claimed in claim 78, wherein the polymer is a homo- or copolymer.

81. The polymer as claimed in claim 78, wherein the polymer is soluble in organic solvents.

82. An electrical component comprising at least one polymer as claimed in claim 78.

83. A compound of the formula (II)

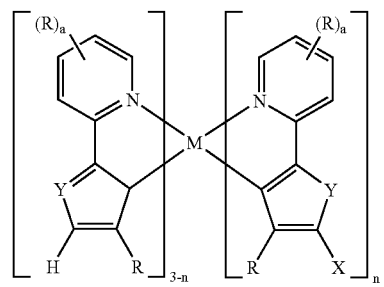

(II)

wherein

M is Rh or Ir,

X, is the same or different and is F, Cl, Br or I,

Y is the same or different and is 0, S or Se,

R is the same or different at each occurrence and is H, F, Cl, Br, $NO_2$, CN, a straight-chain or branched or cyclic alkyl or alkoxy group which has from 1 to 20 carbon atoms and in which one or more nonadjacent $CH_2$ groups is optionally replaced by —O—, —S—, —$NR^1$— or —$CONR^2$— and in which one or more hydrogen atoms in said alkyl or alkoxy group is optionally replaced by F, or an aryl or heteroaryl group having from 4 to 14 carbon atoms which is optionally substituted by one or more nonaromatic R radicals; and a plurality of R substituents, either on the same ring or on the two different rings in the same ligand together in turn optionally encompasses a further monocyclic carbon ring system;

$R^1$ and $R^2$ are the same or different and are each H or an aliphatic or aromatic hydrocarbon radical having 1 to 20 carbon atoms, a is the same or different and is 0, 1, 2, 3 or 4, and n is 1, 2 or 3.

* * * * *